(12) United States Patent
Singh

(10) Patent No.: US 10,898,242 B2
(45) Date of Patent: Jan. 26, 2021

(54) SURGICAL DEVICES FOR SMALL BONE FRACTURE SURGERY

(71) Applicant: Glenhurst Labs, LLC, Belmont, CA (US)

(72) Inventor: Anshuman Singh, San Diego, CA (US)

(73) Assignee: Glenhurst Labs, LLC, Belmont, CA (US)

(*) Notice: Subject to any disclaimer, the term of this patent is extended or adjusted under 35 U.S.C. 154(b) by 0 days.

(21) Appl. No.: 16/066,623

(22) PCT Filed: Dec. 28, 2016

(86) PCT No.: PCT/US2016/068959
§ 371 (c)(1),
(2) Date: Jun. 27, 2018

(87) PCT Pub. No.: WO2017/117263
PCT Pub. Date: Jul. 6, 2017

(65) Prior Publication Data
US 2019/0117282 A1 Apr. 25, 2019

Related U.S. Application Data

(60) Provisional application No. 62/272,034, filed on Dec. 28, 2015.

(51) Int. Cl.
*A61B 17/72* (2006.01)
*A61B 17/16* (2006.01)

(52) U.S. Cl.
CPC ........ *A61B 17/7291* (2013.01); *A61B 17/164* (2013.01); *A61B 17/7241* (2013.01); *A61B 17/7266* (2013.01); *A61B 17/7283* (2013.01); *A61B 17/7233* (2013.01)

(58) Field of Classification Search
CPC ............................................ A61B 17/72–7291
See application file for complete search history.

(56) References Cited

U.S. PATENT DOCUMENTS 2,536,964 A * 1/1951 Stephens .............. A61B 17/742
606/67
2,781,758 A * 2/1957 Chevalier ................. A61F 2/36
623/23.28

(Continued)

FOREIGN PATENT DOCUMENTS

| CN | 103654929 A | 3/2014 |
|---|---|---|
| WO | WO 2013/103261 A1 | 7/2013 |
| WO | WO 2015/090954 A1 | 6/2015 |

OTHER PUBLICATIONS

International Search Report and Written Opinion received in PCT Patent Application No. PCT/US2016/068959 dated Jun. 22, 2017 in 18 pages.

*Primary Examiner* — Ellen C Hammond
(74) *Attorney, Agent, or Firm* — Knobbe, Martens, Olson & Bear, LLP

(57) ABSTRACT

Small bone surgical nail devices and methods for use in small bone fracture surgeries, for example, clavicle fracture surgery. The systems and methods can include a nail device with specific design features including but not limited to differing designs, geometries, and configurations in multiple zones of the device, an associated optional end cap, and/or optional locking screws.

21 Claims, 31 Drawing Sheets

(56) References Cited

U.S. PATENT DOCUMENTS

| | | | | |
|---|---|---|---|---|
| 4,055,172 A | * | 10/1977 | Ender | A61B 17/7208 606/62 |
| 4,135,507 A | * | 1/1979 | Harris | A61B 17/7208 606/62 |
| 4,503,847 A | * | 3/1985 | Mouradian | A61B 17/7208 606/64 |
| 4,561,432 A | * | 12/1985 | Mazor | A61B 17/1721 606/68 |
| 4,630,601 A | * | 12/1986 | Harder | A61B 17/921 606/62 |
| 4,805,607 A | * | 2/1989 | Engelhardt | A61B 17/72 606/64 |
| 4,875,474 A | * | 10/1989 | Border | A61B 17/72 606/63 |
| 4,944,742 A | | 7/1990 | Clemow et al. | |
| 5,035,697 A | * | 7/1991 | Frigg | A61B 17/72 606/329 |
| 5,066,296 A | * | 11/1991 | Chapman | A61B 17/72 606/64 |
| 5,643,258 A | * | 7/1997 | Robioneck | A61B 17/60 606/54 |
| 5,681,289 A | * | 10/1997 | Wilcox | A61B 17/60 604/175 |
| 5,697,930 A | * | 12/1997 | Itoman | A61B 17/72 606/62 |
| 5,766,174 A | * | 6/1998 | Perry | A61B 17/1725 606/62 |
| 6,270,499 B1 | | 8/2001 | Leu et al. | |
| 7,041,106 B1 | | 5/2006 | Carver et al. | |
| 7,846,162 B2 | | 12/2010 | Nelson et al. | |
| 8,021,367 B2 | | 9/2011 | Bourke et al. | |
| 8,287,539 B2 | | 10/2012 | Nelson et al. | |
| 8,357,162 B2 | | 1/2013 | Frake | |
| 8,435,272 B2 | * | 5/2013 | Dougherty | A61B 17/7291 606/329 |
| 8,663,224 B2 | * | 3/2014 | Overes | A61B 17/164 606/62 |
| 8,961,516 B2 | | 2/2015 | Nelson et al. | |
| 9,861,402 B2 | * | 1/2018 | Medoff | A61B 17/1725 |
| 2005/0027294 A1 | * | 2/2005 | Woll | A61B 17/7291 606/62 |
| 2005/0065528 A1 | * | 3/2005 | Orbay | A61B 17/1725 606/62 |
| 2005/0216007 A1 | * | 9/2005 | Woll | A61B 17/7225 606/62 |
| 2006/0036248 A1 | * | 2/2006 | Ferrante | A61B 17/7225 606/64 |
| 2006/0084997 A1 | * | 4/2006 | Dejardin | A61B 17/1725 606/62 |
| 2006/0200142 A1 | * | 9/2006 | Sohngen | A61B 17/72 606/62 |
| 2007/0173834 A1 | * | 7/2007 | Thakkar | A61B 17/7208 606/62 |
| 2008/0027559 A1 | * | 1/2008 | Crowninshield | A61F 2/38 623/23.44 |
| 2008/0125818 A1 | * | 5/2008 | Sidebotham | A61B 17/72 606/329 |
| 2009/0062797 A1 | * | 3/2009 | Huebner | A61B 17/7225 606/62 |
| 2010/0082068 A1 | * | 4/2010 | Graham | A61B 17/7233 606/280 |
| 2010/0114097 A1 | * | 5/2010 | Siravo | A61B 17/686 606/62 |
| 2010/0211073 A1 | * | 8/2010 | Merrell | A61B 17/7225 606/62 |
| 2010/0262197 A1 | * | 10/2010 | Dougherty | A61B 17/7241 606/329 |
| 2010/0305623 A1 | * | 12/2010 | Klaue | A61B 17/72 606/329 |
| 2011/0009865 A1 | * | 1/2011 | Orfaly | A61B 17/1717 606/62 |
| 2011/0087227 A1 | * | 4/2011 | Mazur | A61B 17/68 606/62 |
| 2012/0226326 A1 | * | 9/2012 | Overes | A61B 17/164 606/329 |
| 2013/0035689 A1 | * | 2/2013 | Nanavati | A61B 17/7208 606/62 |
| 2013/0053847 A1 | * | 2/2013 | Siravo | A61B 17/7241 606/62 |
| 2014/0188113 A1 | | 7/2014 | Overes et al. | |
| 2014/0277554 A1 | * | 9/2014 | Roman | A61F 2/4225 623/21.19 |
| 2014/0309747 A1 | * | 10/2014 | Taylor | A61F 2/42 623/21.11 |
| 2015/0374411 A1 | * | 12/2015 | Ehmke | A61B 17/686 606/329 |
| 2016/0015437 A1 | * | 1/2016 | Elleby | A61B 17/7291 606/329 |
| 2016/0081728 A1 | * | 3/2016 | McCormick | A61B 17/1604 606/64 |
| 2016/0317200 A1 | * | 11/2016 | Hoogervorst | A61B 17/7233 |
| 2017/0014170 A1 | * | 1/2017 | Fallin | A61B 17/863 |
| 2017/0112552 A1 | * | 4/2017 | Sinnott | A61B 17/7233 |
| 2019/0069936 A1 | * | 3/2019 | Mirza | A61B 17/7283 |

\* cited by examiner

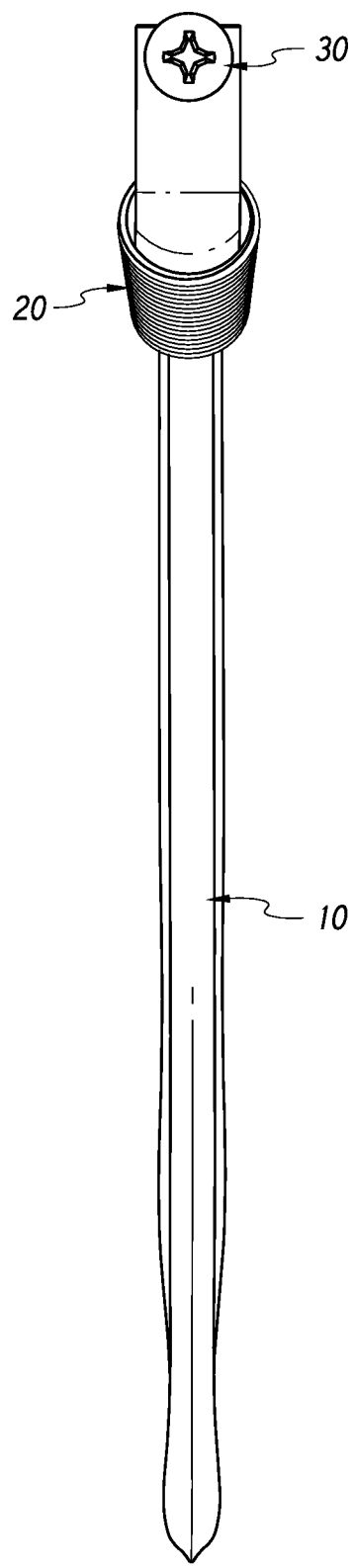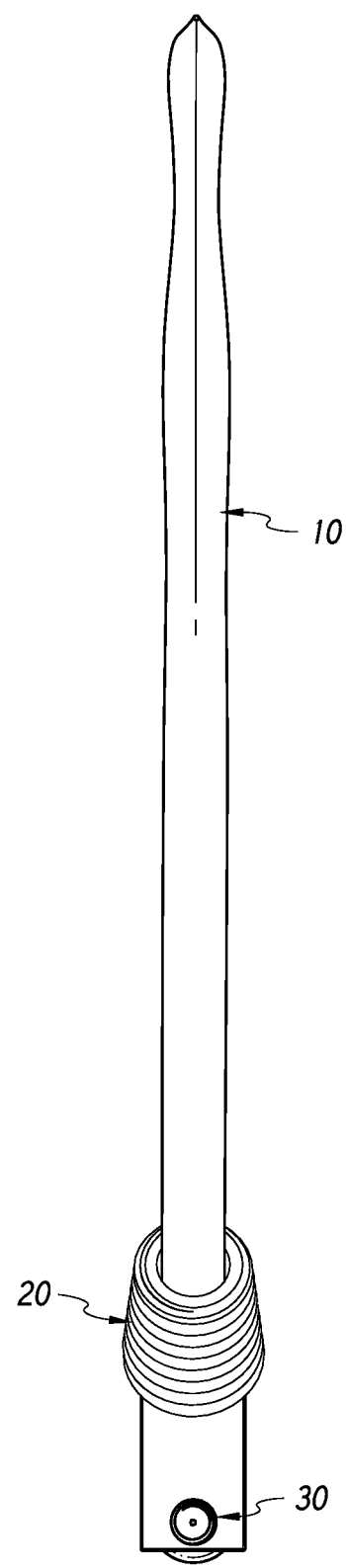
FIG. 3F
FIG. 3G

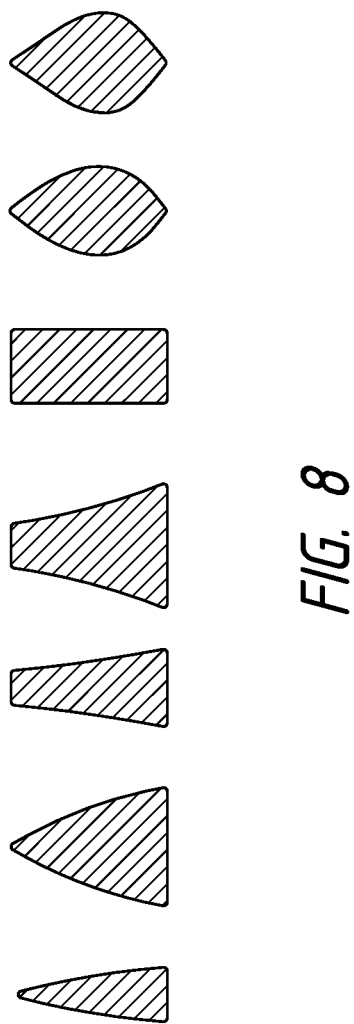

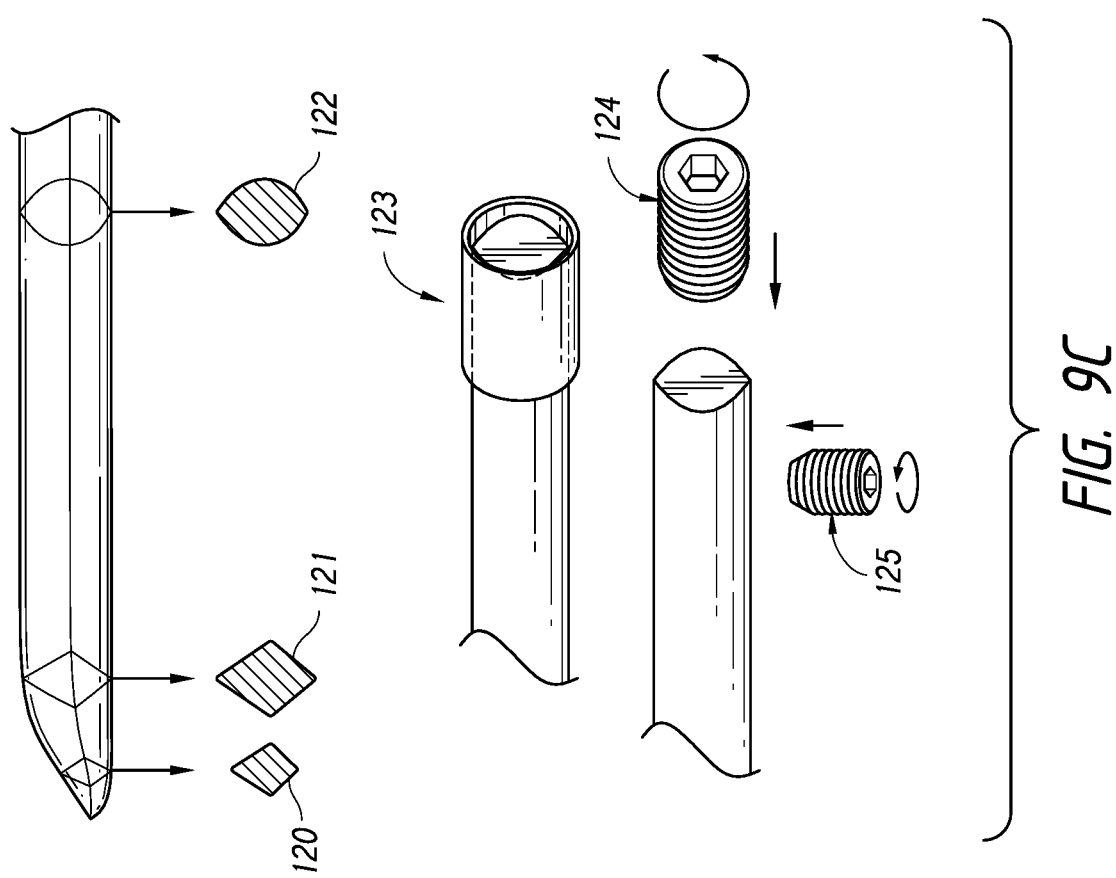

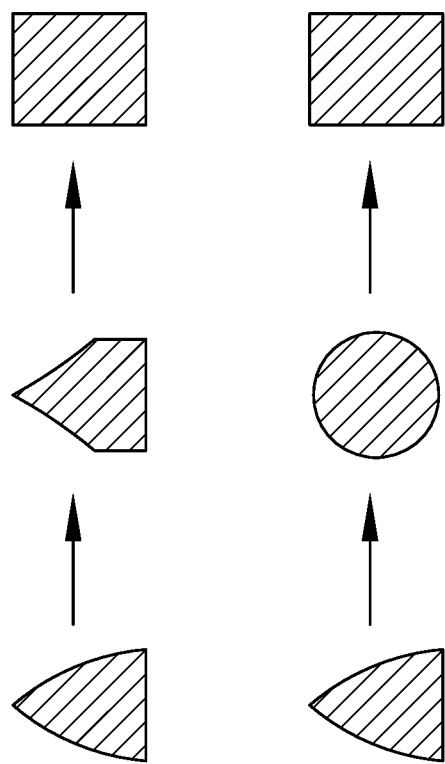

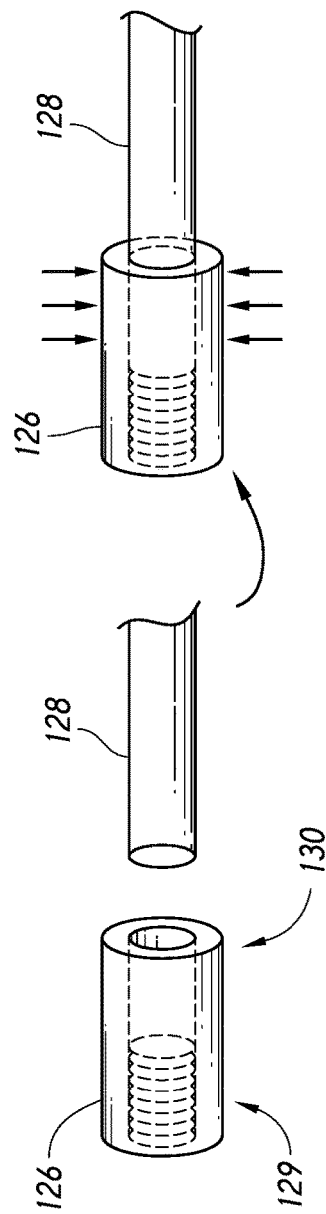
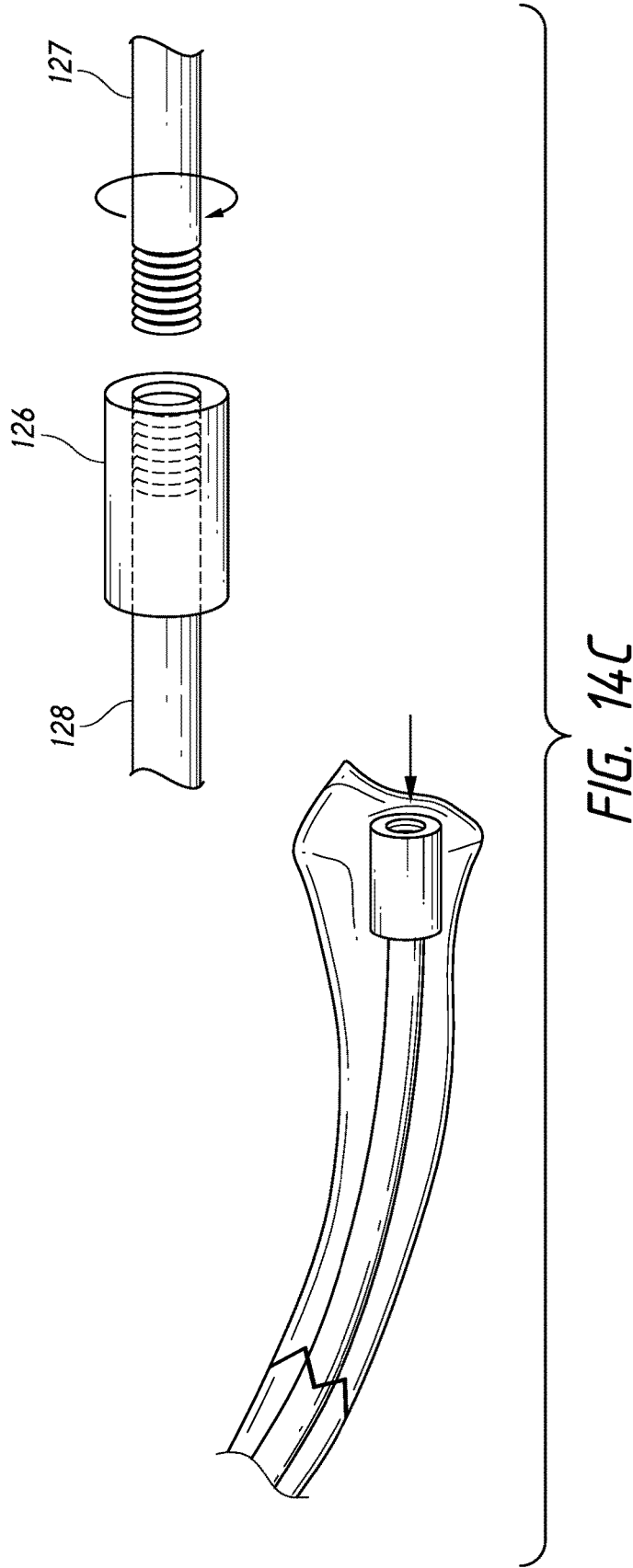
FIG. 14B
FIG. 14C

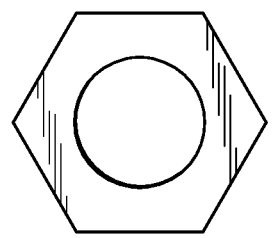
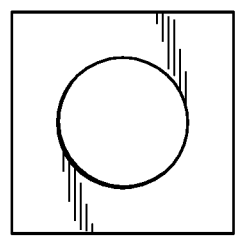
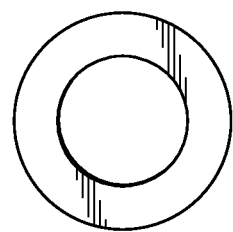
FIG. 14D

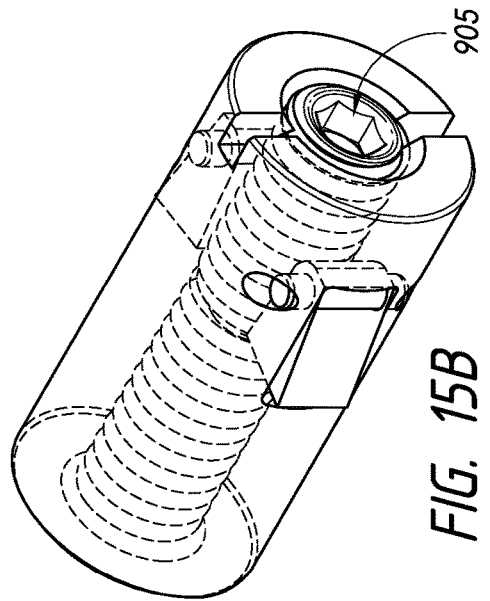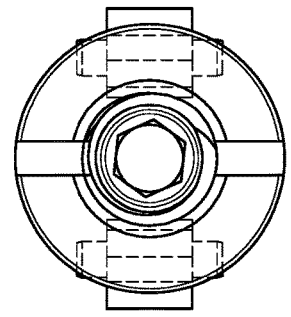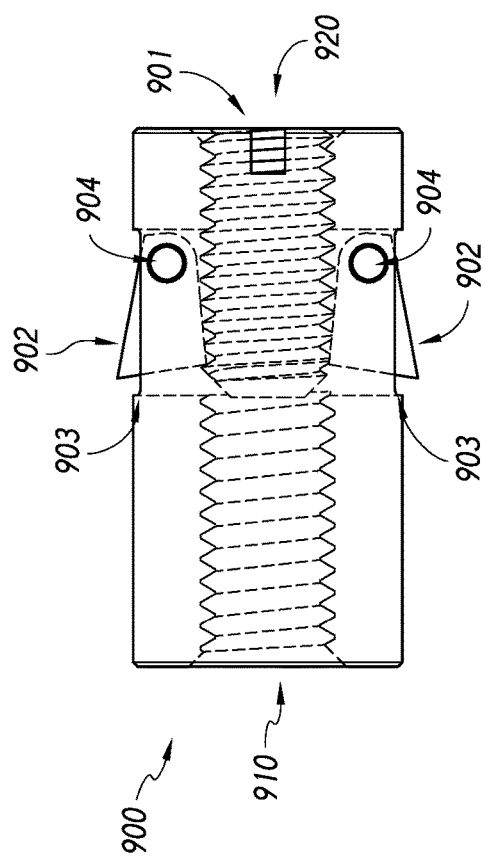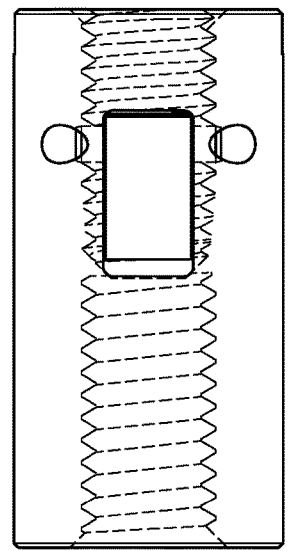
FIG. 15B
FIG. 15D
FIG. 15A
FIG. 15C

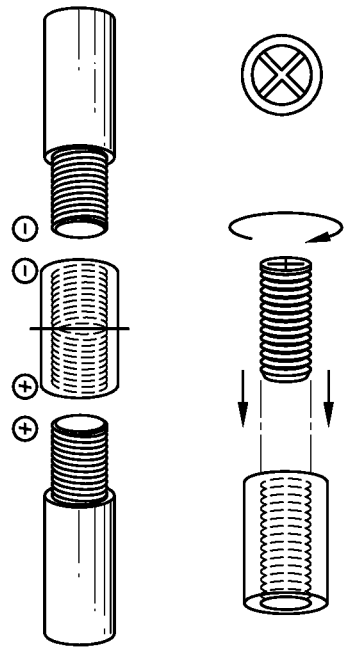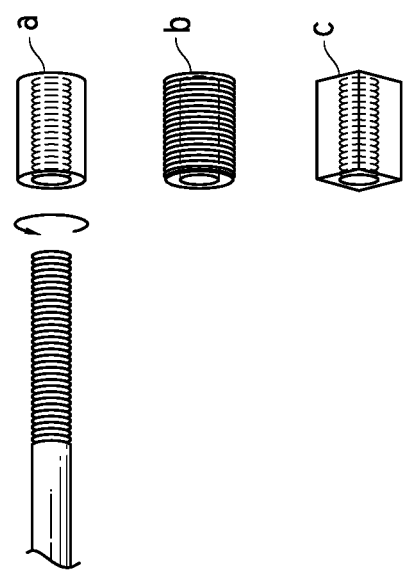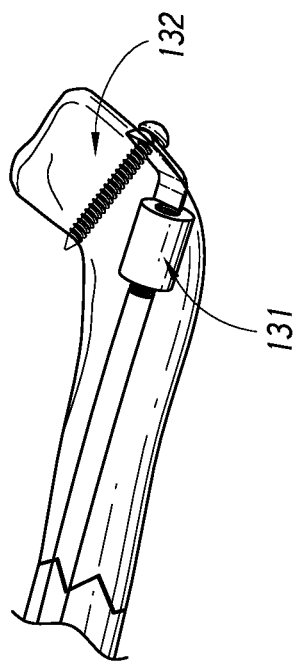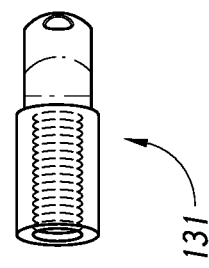
FIG. 18A
FIG. 18B
FIG. 18C

SURGICAL DEVICES FOR SMALL BONE FRACTURE SURGERY

BACKGROUND

Technical Field

Embodiments described herein relate to innovative surgical devices and methods that can be used to significantly improve clinical outcomes for patients while reducing healing times, reducing costs, and increasing surgical accuracy in small bone fracture surgeries. Embodiments of small bone surgical devices and methods can be particularly impactful on small bone fracture surgeries, including, but not limited to, clavicle fracture surgery.

Background

Fractures of small bones, for example, clavicle fractures, are common and may require surgery. Clavicle fractures are one of the most common fractures. However, current repair devices are insufficient. The devices used to repair clavicle fractures or other small bone fractures include either nails or plates. Plates can be large and overbearing and can protrude from the skin. This can cause large incisions and scars which can lead to numbness and tingling post-surgery. Additionally, removing a plate post-surgery is very difficult. It can require longer procedures that are more expensive for every party involved. Current nail products can be difficult to place and, after inserted, too often need to be removed. More importantly, they can move excessively within the bone (e.g., migration, rotation).

SUMMARY

Certain embodiments of the application address a need for a surgical nail system that will prevent migration and rotation while allowing for ease and efficiency of insertion. In some aspects, a clavicle nail fixation system is provided, the system comprising a nail sized for positioning within a clavicle bone. The nail comprises an elongate shaft having a proximal end and a distal end, the nail comprising multiple zones along its length having various cross-sectional geometries.

The system of the preceding paragraph may also include any combination of the following features described in this paragraph, among others described herein. The system can include the nail comprising an end zone at its distal end having a first cross-sectional shape and a shaft zone proximal to the end zone having a second cross-sectional shape, wherein the first cross-sectional shape is different from the second cross-sectional shape. The system can include a transition zone between the end zone and the shaft zone, wherein the transition zone has a third cross-sectional shape. The system can include at least the end zone having a non-circular cross section. The system can include the end zone, transition zone, and shaft zone comprising a non-circular cross section. In some embodiments, the shaft zone has a larger cross-sectional area than the end zone. In some embodiments, the shaft zone has a cross sectional area greater than or equal to a cross sectional area of the transition zone and wherein the cross sectional area of the transition zone is greater than or equal to a cross sectional area of the end zone. In some embodiments, the proximal end of the nail has a round-cross section. In some embodiments, the nail comprises an anterior surface sized and configured to face an anterior side of the clavicle bone and a posterior surface sized and configured to face a posterior side of the clavicle bone, and wherein the nail is bent or curved toward either the anterior surface or the posterior surface. In some embodiments, at least a portion of either the anterior surface or the posterior surface is flat. In some embodiments, the distal end of the nail has at least one sharp edge. In some embodiments, the end zone comprises a cutting geometry configured to create a path through the medullary canal of the bone, the cutting geometry comprising a curvature on at least one edge of the end zone toward the distal end of the device configured to create a sharp distal end. In some embodiments, a distal portion of the nail has a cross-section with four flat sides. In some embodiments, the nail has a first cross-section with a plurality of flat surfaces and a second cross-section with a single flat surface, wherein the second cross section is proximal to the first cross-section. In some embodiments, the transition zone is configured to provide at least one transitional cross section between the first cross-section with a plurality of flat surfaces and the second cross-section with a single flat surface. The system can include an end cap at or configured to engage the proximal end of the nail. In some embodiments, the proximal end of the nail is externally threaded and a distal portion of the end cap is internally threaded for attachment to the externally threaded proximal end. In some embodiments, the end cap is crimped or welded onto the proximal end of the nail. In some embodiments, the end cap comprises a plurality of retractable and expandable wings for engagement with bone. In some embodiments, a proximal portion of the end cap is internally threaded to receive a screw extractor. The system can include one or more locking screws for engagement with the end cap or the nail.

In some aspects, a surgical device for use in small bone fracture surgery comprises a surgical nail configured to be at least partially submerged within a bone, the surgical nail comprising a distal end and a proximal end, the surgical nail comprising a first zone positioned at the distal end of the surgical nail configured to be inserted into bone, the first zone comprising a non-circular cross section, the first zone having a first cross-sectional area, wherein the first zone comprises a cutting geometry configured to create a path through the medullary canal of the bone, the cutting geometry comprising a curvature on at least one edge of the first zone toward the distal end of the device configured to create a sharp distal end; a second zone comprising a non-circular cross section and positioned proximal to the first zone, the second zone comprising a second cross-sectional area, and a third zone comprising a non-circular cross section and positioned proximal to the second zone, the third zone comprising a third cross sectional area, wherein the third cross sectional area comprises at least one flat edge configured to allow the third zone to engage with the surrounding bone, wherein the second zone is configured to provide at least one transitional cross section between the sharp distal end and the at least one flat edge of the third zone, and wherein the third cross-sectional area is greater than or equal to the second cross sectional area and the second cross sectional area is greater than or equal to the first cross sectional area.

BRIEF DESCRIPTION OF THE DRAWINGS

Various embodiments of the devices and methods of the present disclosure are described herein with reference to the drawings wherein:

FIGS. 3A-G illustrate views of an embodiment of a small bone fracture system including a nail, end cap, and locking screw system;

FIG. 8 illustrates cross-sections of the end zone of the device that can be used:

FIG. 9C illustrate embodiments of a surgical nail system;

FIGS. 11A-B show embodiments of the transition from the sharp to flat cross-section of the small bone surgical nail device;

FIG. 14B illustrates an embodiment of the end cap including an extraction end cap that has a screw pitch for later extraction:

FIG. 14C illustrates an embodiment of the end cap that can allow for extraction by a screw-in attachment;

FIG. 14D illustrates embodiments of alternate cross sectional geometries for the end cap;

FIG. 15A-D illustrates views of an embodiment of the end cap design with locking wings;

FIG. 18A-C illustrates embodiments of the end cap designs for the small bone surgical nail system;

DETAILED DESCRIPTION

Figure 1:
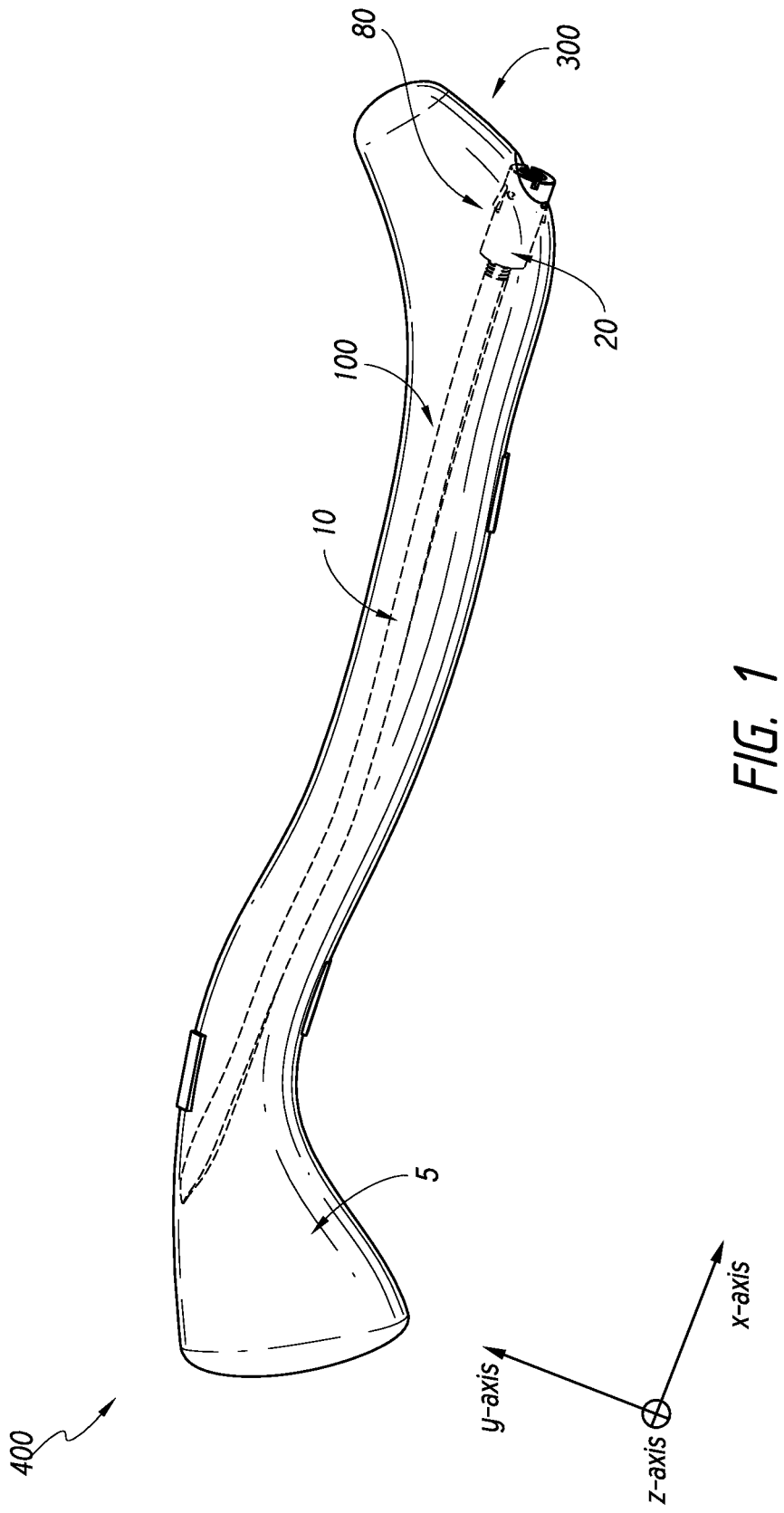
FIG. 1 illustrates an embodiment of a small bone fracture system including a nail, end cap, and locking system within a clavicle bone.

Embodiments of the small bone surgical nail system can be used for small bone fracture surgeries, for example clavicle fracture surgery. The small bone surgical nail systems disclosed can be used in whole or in part, with each element or aspect of the system being independently applicable of each other. The system comprises a nail device with specific design features including but not limited to differing designs, geometries, and configurations in multiple zones of the device, an associated optional end-cap, and/or optional locking screws or locking systems. In some embodiments, the nail device can be made of a material used for surgical implants and surgical nails including, but not limited to, stainless steel and titanium and alloys thereof.

The small bone surgical nail system can have multiple zones as shown in at least FIGS. 1, 2, FIGS. 3A-G. FIGS. 4A-G, FIG. 5, FIG. 6, and FIG. 7. As illustrated in these figures, in some embodiments the device can vary in three distinct zone types: the end zone; the transition zone: and the shaft zone. The distinct zones can have unique geometries that can facilitate insertion, improve rotational control, simplify extraction, create flexible lengths, and increase stability of the device. The multiple zone device design, with particular attention to minor design details in each zone, is advantageous for small bone surgeries within which the surgeon must operate with a small margin for error around limited space and bone. As described further below, zones can be used in varying order and numbers, but describe the innovative design structure of a given nail system that provide improved surgical results on many levels. As one example, the end zone of the device can comprise a distal end or distal tip of the device and is the first portion introduced into bone. The end zone can be the leading end as the device is passed through the bone, which may be proximal to a shaft zone. A transition zone may be positioned between any two zones, for example, between the end zone and a shaft zone.

The small bone surgical nail system utilizes the device geometry within different zones within the device that are designed to optimize surgery. In some embodiments, the nail device can include at least two zones. The design of the nail is based on the individual zones as well as how each zone of the device works with respect to one another (and hence, impacts surgery and healing). Described herein is a device with three or more zones, however, the device can be made of any number of zones greater than one.

Although not limited to this geometry, at least the first two zones (distal zones, e.g., the end zone and the transition zone) of the device can have non-circular cross-sections. In some embodiments, all zones contain non-circular cross-sections. In some embodiments, along the length of the nail from a distal end to a proximal end the cross-sectional area of each zone is greater than or equal to the cross-sectional area of the more distal zone. Depending on the bone or fracture being repaired, the nail can be entered through various positions within the body. For example, to repair a clavicle fracture, it is understood that the nail may enter the fractured clavicle from either the distal end of the clavicle at the shoulder or the proximal end of the clavicle at the sternum.

FIG. 1 illustrates a view of an embodiment of the small bone fracture system including a nail 10, an end cap 20 at a proximal end of the nail 10, and the end cap has a winged locking system 80 within a clavicle bone 5. As illustrated, the distal tip of the nail 10 is positioned on the lateral side of the clavicle bone 5, and the proximal end of the nail 10 (where the end cap 20 and winged locking system 80 are located) is positioned on the medial side of the clavicle bone 5. The various geometries of the nail 10, as described further below, are positioned in the clavicle bone to prevent rotation and movement within the bone. Additionally, an embodiment of an end cap and winged locking system are also shown positioned within the clavicle bone and attached to the medial or proximal end of the surgical nail. The details of the winged locking system are described in more detail below.

The clavicle bones can also have an anterior side and a posterior side. The posterior side of the clavicle refers to the portion of the clavicle directed toward the back side of the body of the patient. The anterior side of the clavicle refers to the portion of the clavicle directed toward the front side of the body of the patient. The anterior side of the clavicle is the front of the clavicle bone as shown in FIG. 1. The posterior side of the clavicle bone in FIG. 1 is not shown and would be facing into the page. The clavicle bone presents a double curvature. The curvature of the clavicle bone can include a convex anterior curve in the medial half and a concave anterior curve in the lateral half of the clavicle.

Figure 2:
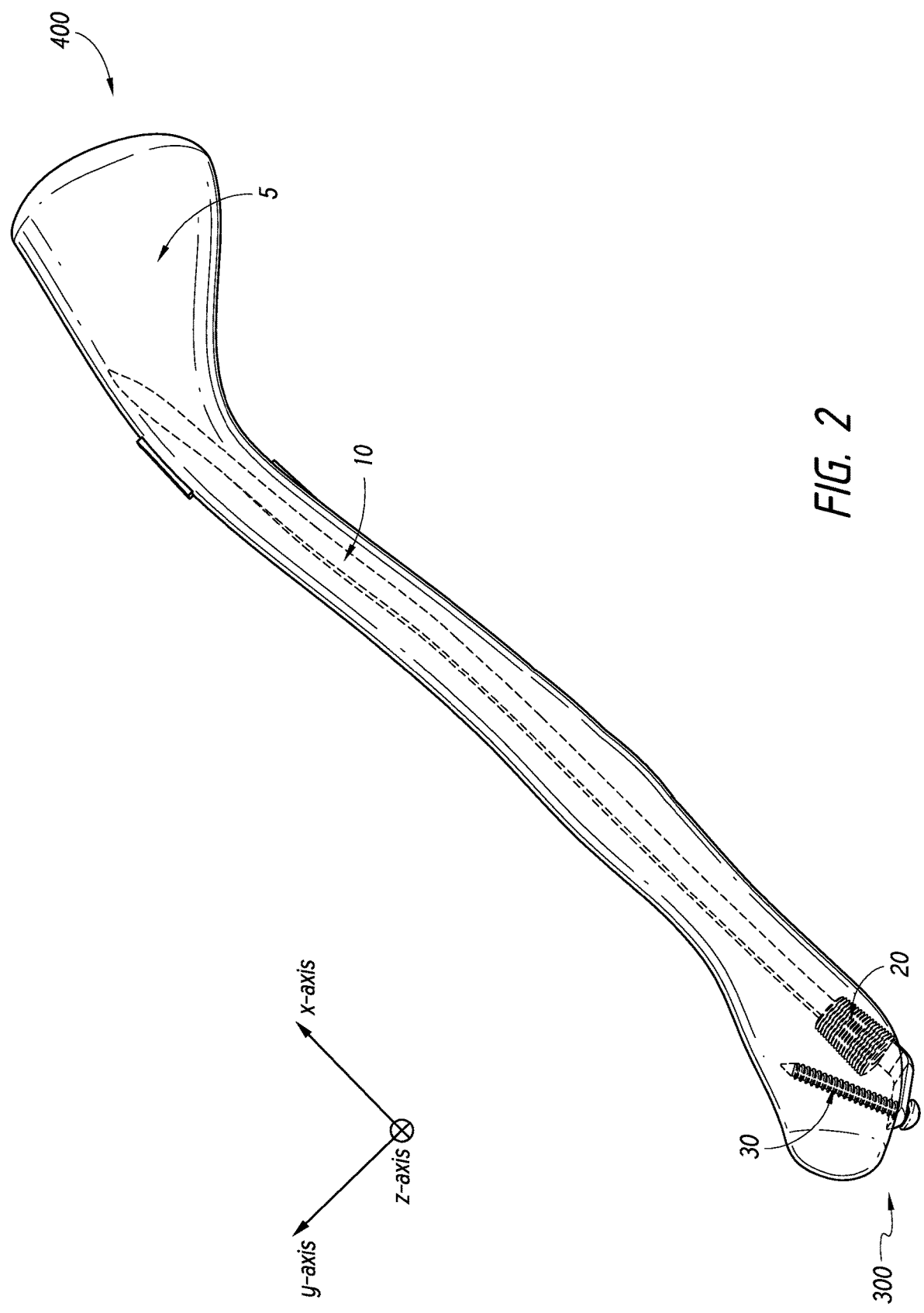
FIG. 2 illustrates of an embodiment of a small bone fracture system including a nail, end cap, and locking system within a clavicle bone.
Figure 3A:
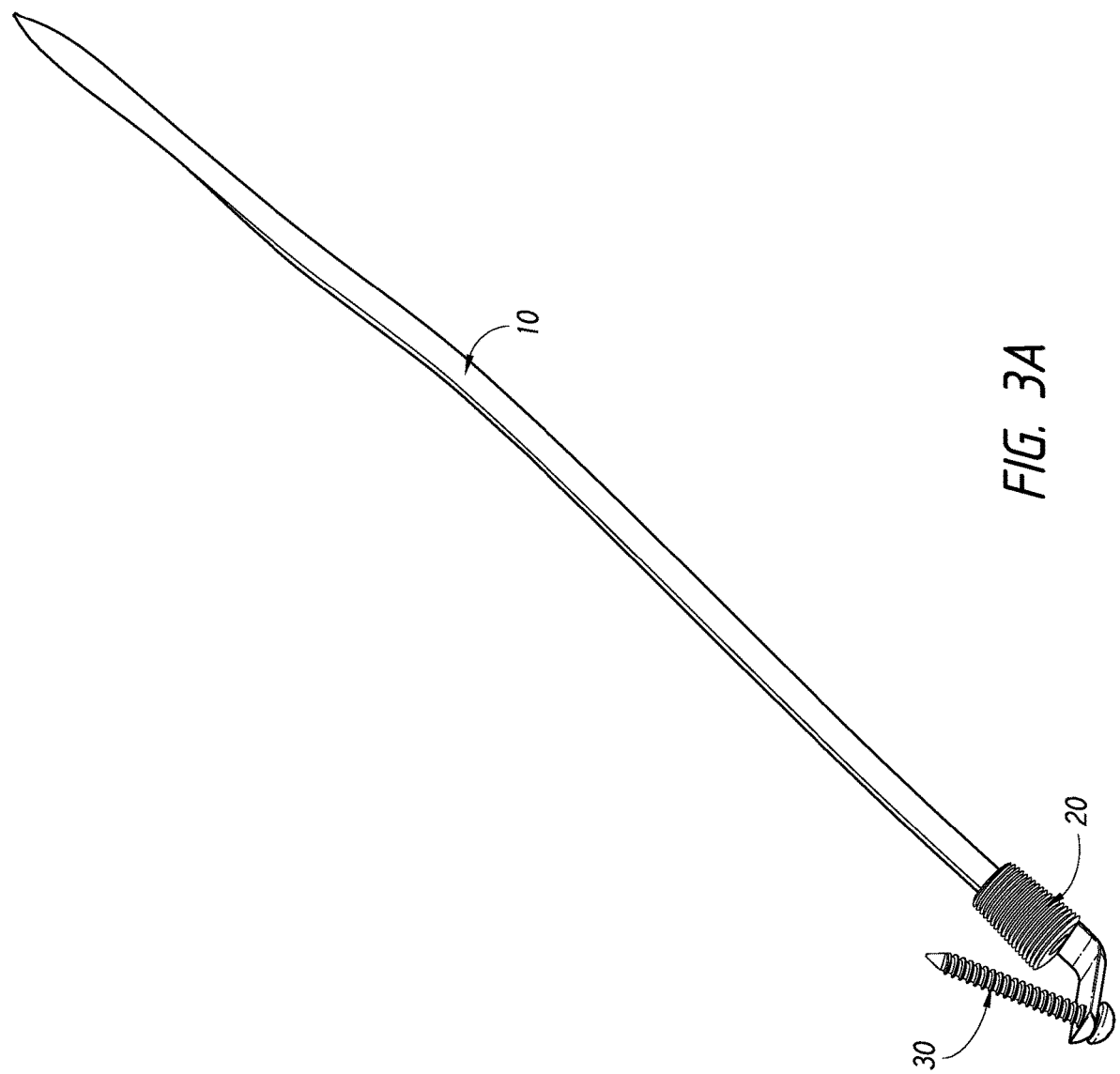
Figure 3B:
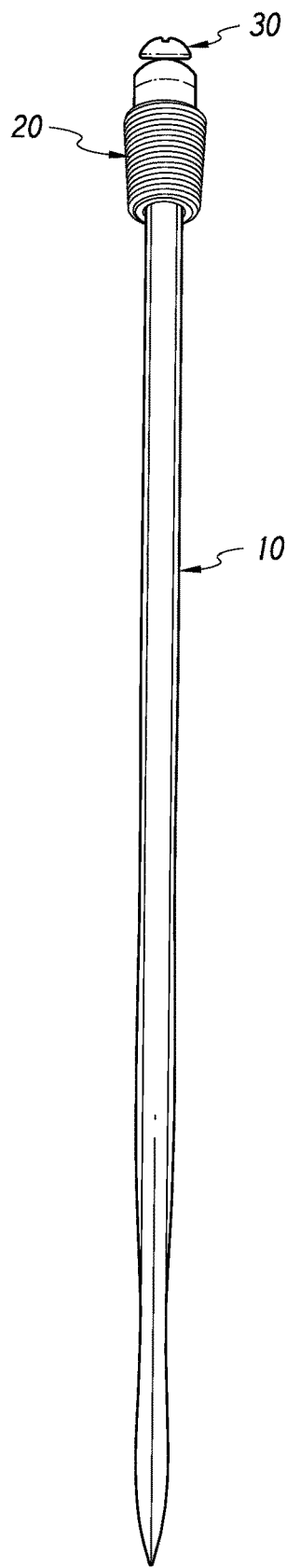
Figure 3C:
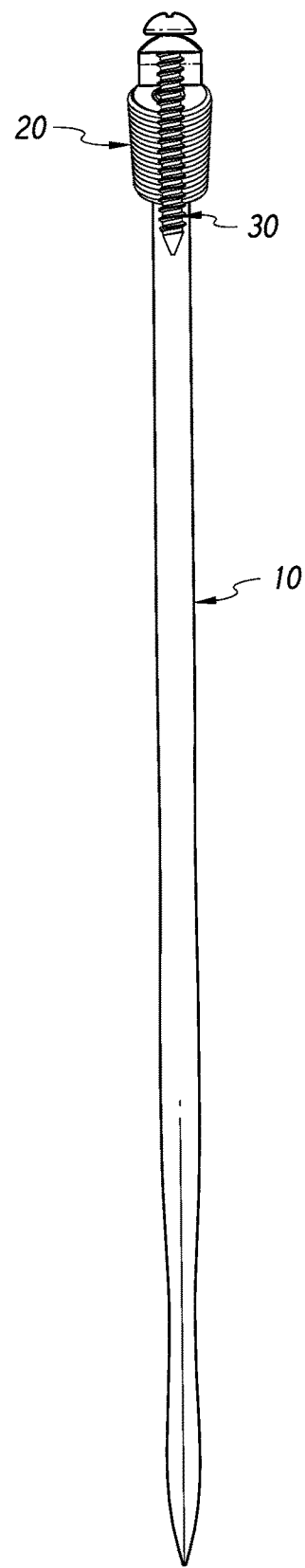
Figure 3D:
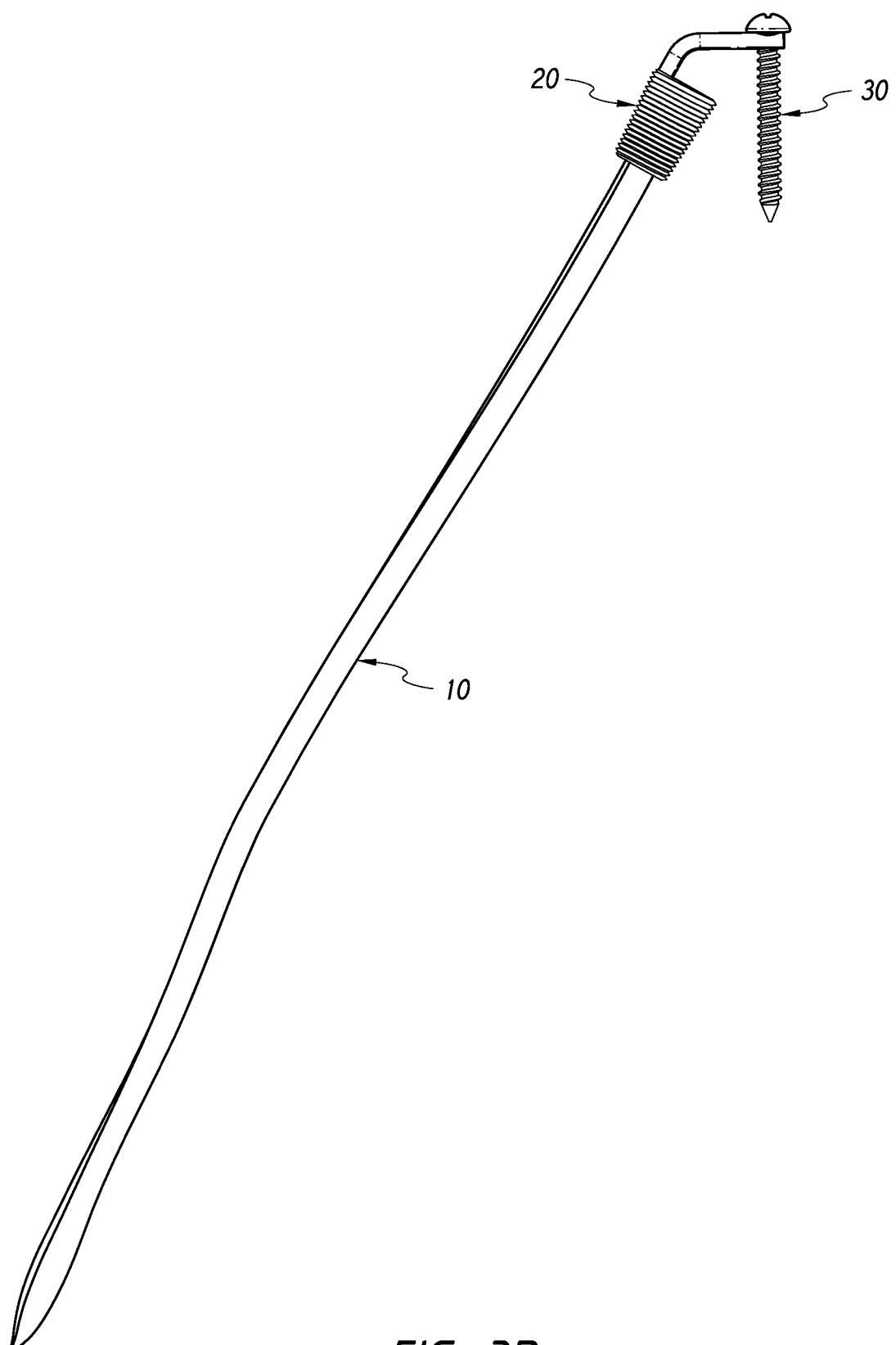
Figure 3E:
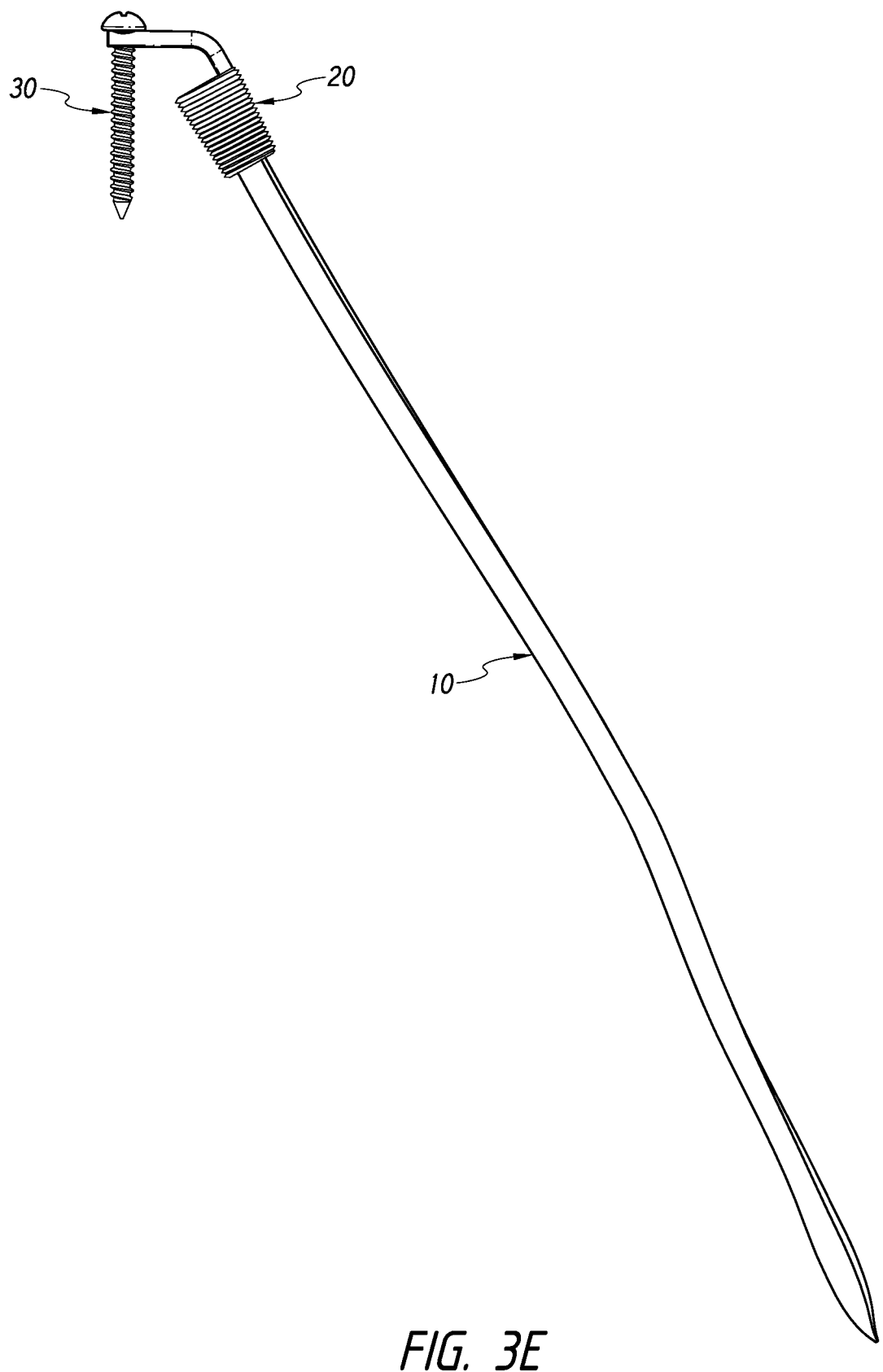
Figure 4A:
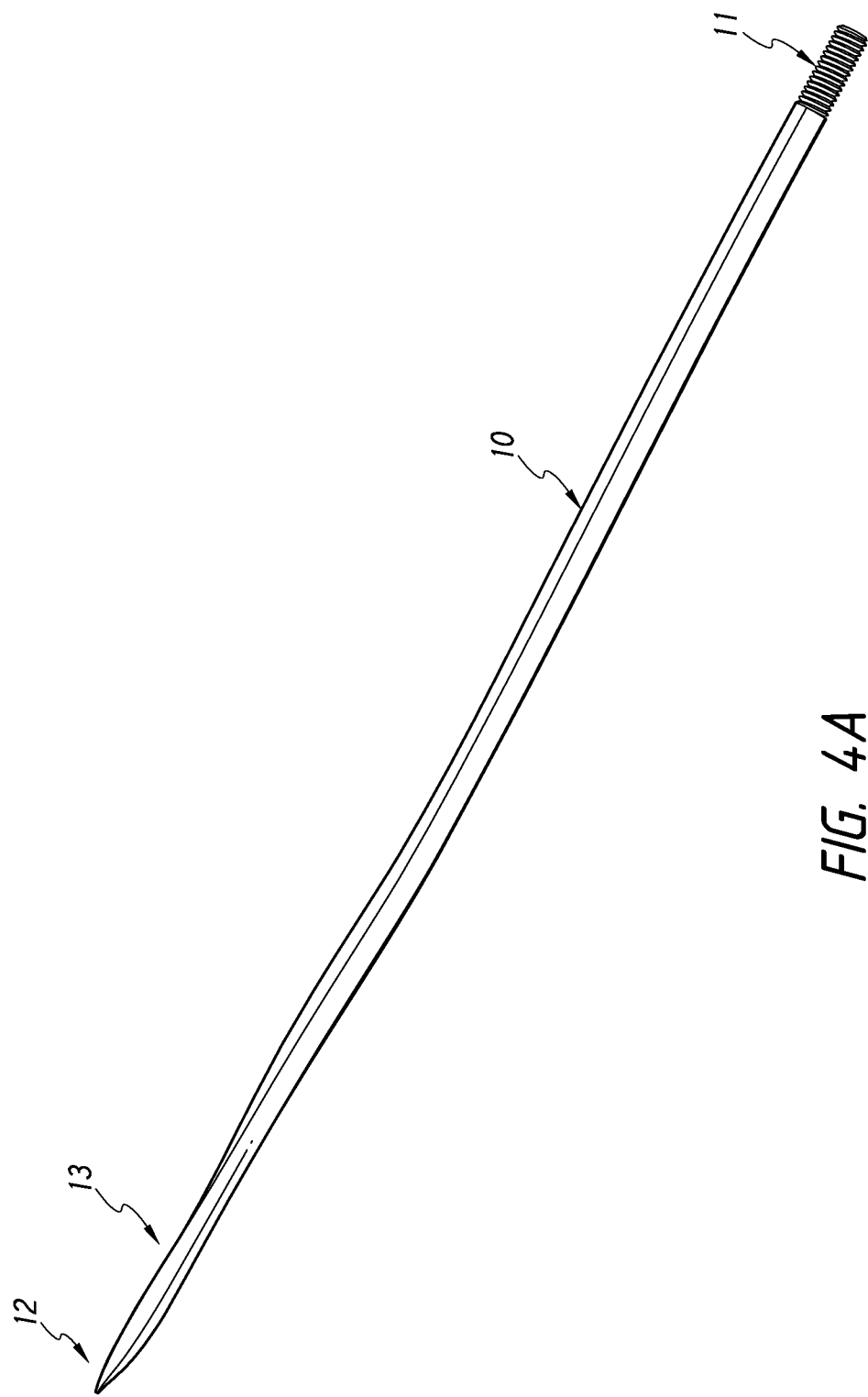
FIGS. 4A-G illustrate views of an embodiment of a surgical nail.
Figure 4B:
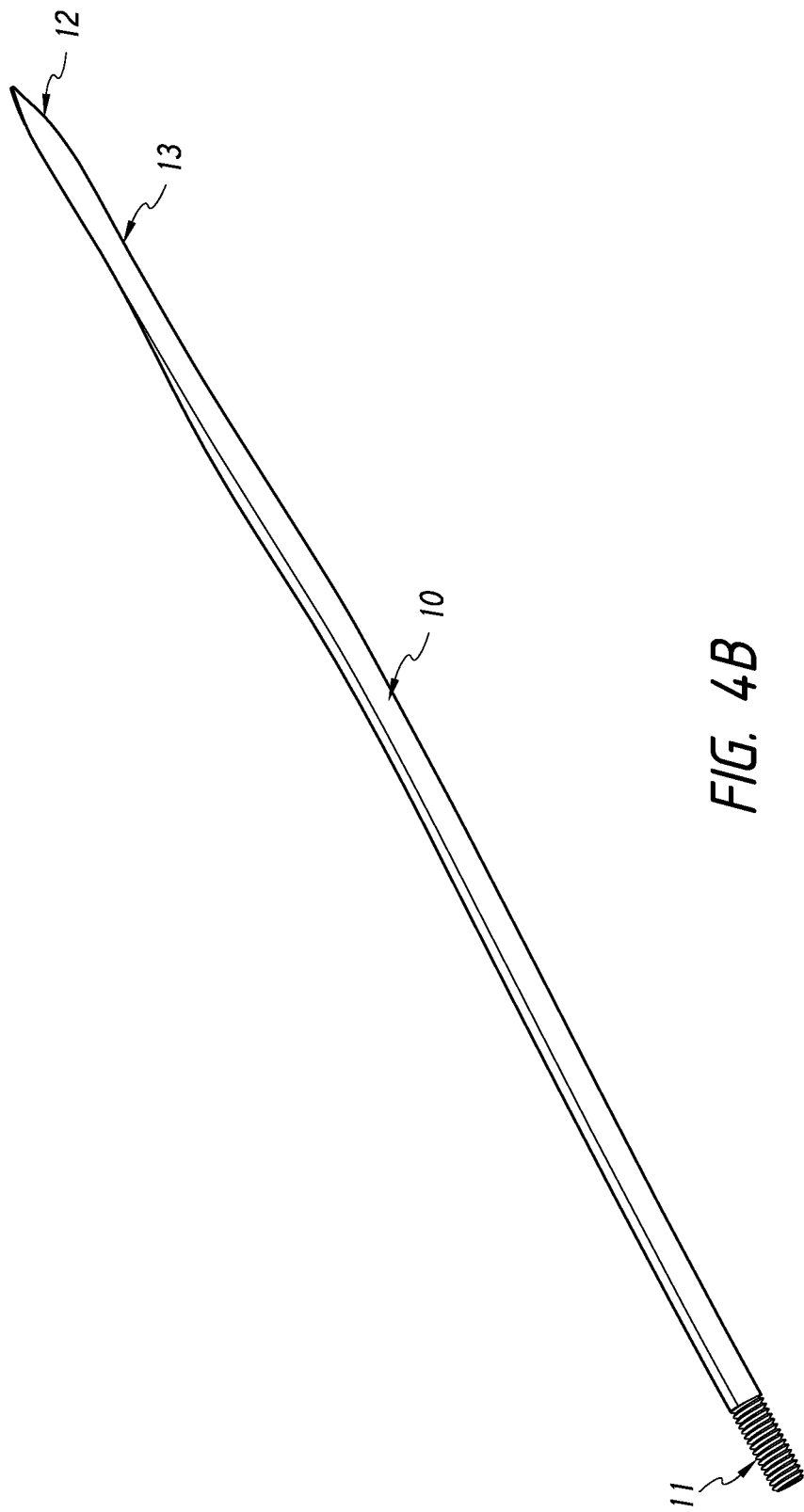
Figure 4C:
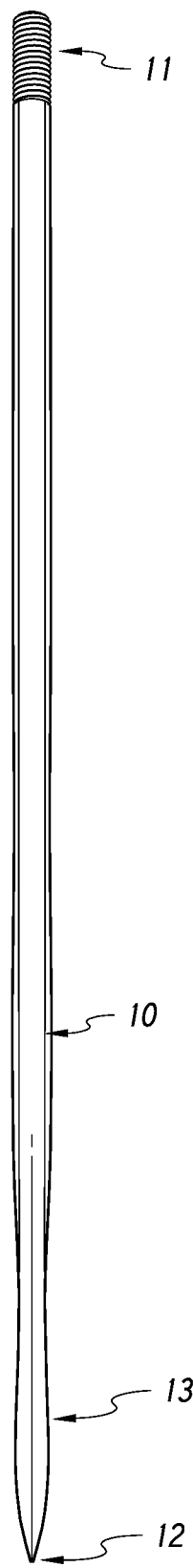
Figure 4D:
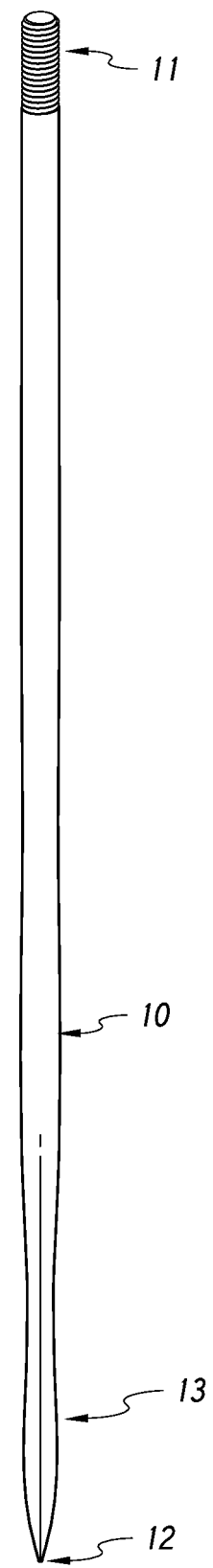
Figure 4E:
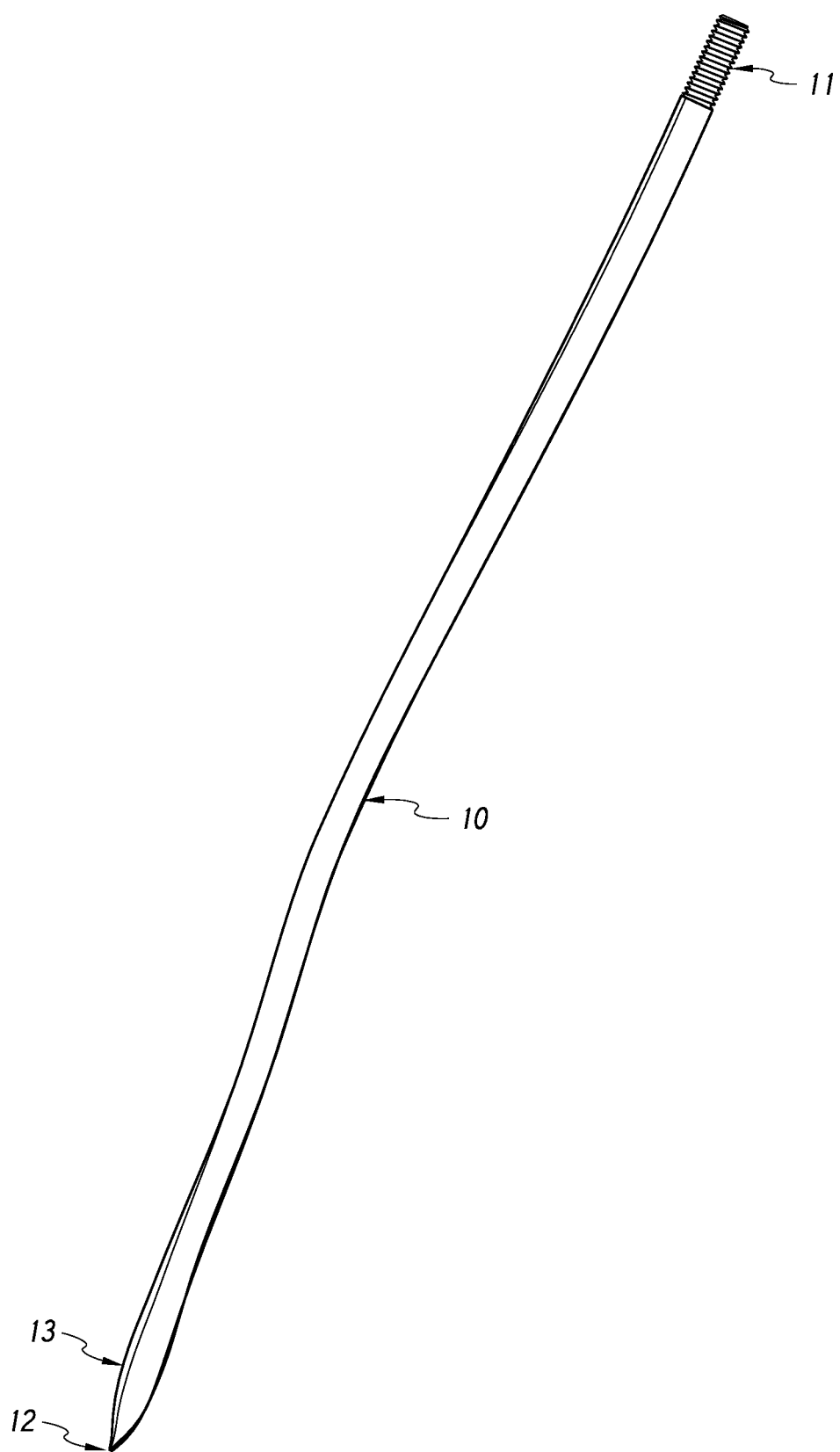
Figures 4F, 4G:
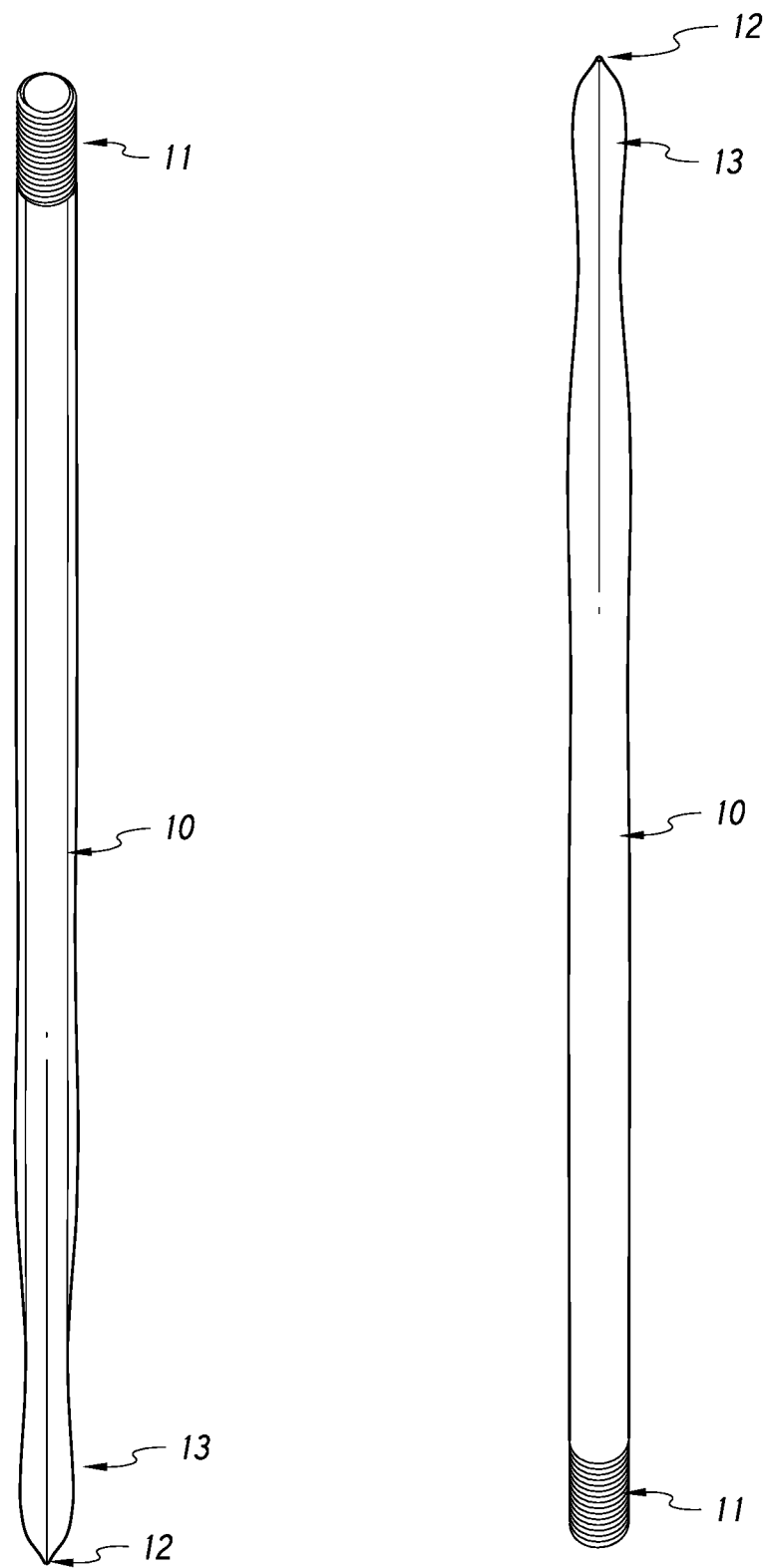

As discussed in more detail below, the surgical nail can have varying geometries that ease insertion and prevent rotation of the surgical nail. In some embodiments, the nail can include flat surfaces. In some embodiments, the flat surfaces can be aligned with and facing the posterior side of the clavicle bone. In some embodiments, the flat surfaces can be aligned with and facing the anterior side of the clavicle bone. In some embodiments, the flat surfaces can be in more than one portion of the nail and at least one flat surface can be aligned with and facing the anterior side of the clavicle bone and at least one flat surface can be aligned with and facing the posterior side of the clavicle bone. The illustrated clavicle bone shown in FIGS. 1 and 2 is shown with the length of the bone aligning with an x-axis and a y-axis is perpendicular to the length of the clavicle bone and passes through the width of the bone from top to bottom. The z-axis passes through an anterior-posterior width of the clavicle bone and as illustrated in FIGS. 1 and 2 the z-axis goes into and out of the page. The clavicle bone has an S-shaped curvature that curves along the z-axis into and out of the page as illustrated in FIGS. 1 and 2. The curvature of the clavicle bone can include a convex anterior curve in the medial half and a concave anterior curve in the lateral half of the clavicle.

As shown in FIGS. 1 and 2, the nail can have an anterior and posterior portion. The posterior portion of the nail refers to the portion of the nail directed toward the back side of the body of the patient when the device is implanted. The anterior portion of the nail refers to the portion of the nail directed toward the front side of the body of the patient when the device is implanted. The shaft of the nail can have an anterior 100 and posterior 200 portion that defines the positioning of the nail within the clavicle bone or other small bone, with the medial end (or proximal end) 300 and the lateral end (or distal end) 400 referring to the lateral side and medial side of the clavicle bone or other small bone. The posterior portion 200 of the nail 10 cannot be seen in FIG. 1 as the posterior portion 200 is facing into the page.

FIG. 2 illustrates another embodiment of the small bone fracture system including a nail 10, an end cap 20 at a proximal end of the nail 10, and locking screw system 30 within a clavicle bone 5. As illustrated, the distal tip of the nail 10 is positioned on the lateral side of the clavicle bone 5, and the proximal end of the nail 10 (where the end cap 20 and locking screw system 30 are located) is positioned on the medial side of the clavicle bone 5. The various geometries of the nail 10, as described further below, are positioned in the clavicle bone to prevent rotation and movement within the bone. Additionally, an embodiment of an end cap and locking screw are also shown positioned within the clavicle bone and attached to the medial or proximal end of the surgical nail. As described previously, depending on the bone or fracture being repaired, the nail can be entered through various positions within the body. For example, to repair a clavicle fracture, it is understood that the nail may enter the fractured clavicle from either the medial end of the clavicle at the sternum as described and shown with reference to FIGS. 1 and 2 previously or the lateral end of the clavicle at the shoulder (not shown). In embodiments where the nail is entered from the lateral end of the clavicle, the nail geometry described herein can be reversed from the proximal to distal end of the nail from that shown and described herein. Therefore, in such embodiments, the components and zones described on the proximal end of the nail would be on the distal end of the nail and the components and zones described on the distal end of the nail would be on the proximal end of the nail. Additionally, in such embodiments, the end cap and lock screw can be positioned at the lateral end of the surgical nail once inserted into clavicle.

FIGS. 3A-G illustrates views of an embodiment of the small bone fracture system described above without the bone 5 being illustrated. As shown by FIGS. 1, 2, 3A-G. and 4A-G the curvature of the nail 20 can be utilized to ease insertion of the nail 20 within the bone 5 with minimal damage to the surrounding bone as well as prevent movement once placed within the bone. In some embodiments, the curvature of the nail can curve along the z-axis, from anterior to posterior and/or posterior to anterior, mimicking the natural S-shaped curve of the clavicle bone. In some embodiments, as shown in FIGS. 3A-G and 4A-G the anterior side of the nail 10 can include a flat surface that faces the anterior surface of the clavicle bone. In some embodiments, the posterior side of the nail can include a flat surface that faces the posterior surface of the clavicle bone. In some embodiments, both the anterior and posterior surfaces of the nail can include a flat surface. The placement of the flat surface on the anterior and/or posterior portions of the nail can ease insertion of the nail into the clavicle bone. The flat surface on the anterior and/or posterior portions of the nail can allow for the nail to bend or curve toward the anterior or posterior surface of the clavicle forming a bend or curve that mimics the S-shaped curvature of the clavicle bone along the z-axis. In some embodiments, the nail is titanium, which is soft and allows the nail to contour to the bone. In some clavicle surgical procedures, the insertion point for the nail can be a bit anterior and lateral to the medial end of the bone. This could put the insertion point mostly past the first curvature of the S shaped clavicle bone. Therefore, in some embodiments, there may only be a need for one bend or curvature in the nail device.

The end cap 20 as shown in FIGS. 3A-G can have a threaded portion in the interior of the end cap as described in more detail below. The proximal end of the nail can also include a threaded portion complementary to the internally threaded portion of the end cap 20. This allows the end cap 20 to be screwed on to the proximal or medial end of the nail 10. The end cap 20 can also include a locking screw 30 to assist in anchoring the surgical nail system in the bone as described in detail herein.

FIGS. 4A-G illustrates further views of an embodiment of the surgical nail as described above. The surgical nail as shown in FIGS. 4A-G comprises an elongated shaft that includes a proximal end 11. In some embodiments, the proximal end 11 can include an externally threaded portion. As illustrated in FIGS. 4A-G, the surgical nail can include a nail tip 12 at the distal most end of the elongated shaft, and a central shaft portion between the proximal and distal ends that includes various curvatures and cross-sections as described in more detail below. For example, a section 13 of the elongated shaft shown in FIGS. 4A-G illustrates a curvature and non-circular cross-section of the nail.

Figure 5:
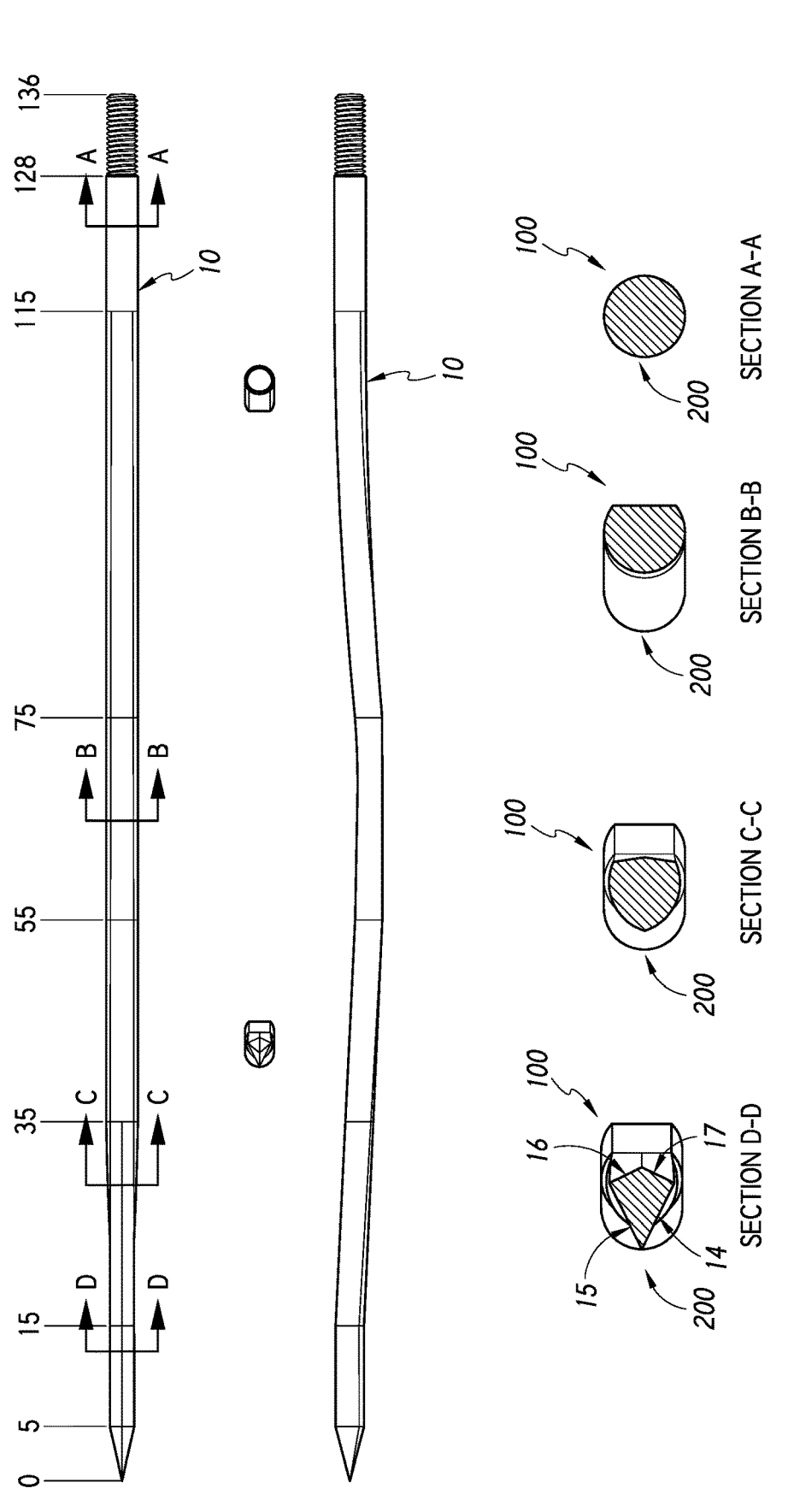
FIG. 5 illustrates views of an embodiment of a surgical nail with cross sections D-D, C-C, B-B, and A-A.

FIG. 5 illustrates views of an embodiment of the surgical nail of FIG. 4A-G with cross sections D-D, C-C, B-B, and A-A shown. Cross section D-D includes a cross section relatively closer to the distal end of the nail 10, and the cross section A-A includes a cross section relatively closer to the proximal end of the nail 10. As can be seen in cross section D-D the non-circular cross-section of the distal end of the nail includes more than one flat end 14, 15, 16, 17. As illustrated in the cross section D-D, the flat ends meet to form sharp points or edges to help tunnel the nail through the bone. This configuration creates an anterior pointed edge 100 and a posterior pointed edge 200 as shown in cross section D-D. Cross section C-C and cross section B-B represent additional cross sections on the nail. Cross section C-C represents a cross section from a more proximal position on the nail than the cross section from cross section D-D and the cross section B-B represents a cross section from a more proximal position on the nail than the cross section C-C. Cross section C-C and cross section B-B includes a cross section with a more rounded shape on the posterior side 200 of the nail than cross section D-D but still maintaining a non-circular cross section with at least one flat side. The cross section C-C represents an intermediate cross section between cross section D-D and cross section B-B and represents the transitional shape between the cross section D-D and cross section B-B. Cross section C-C includes a rounded posterior side 200 of the nail and a flat surface on the anterior side 100 of the nail. Cross section A-A represents a cross section at a proximal end of the nail (more proximal than cross section B-B). Cross section A-A includes a circular cross section. As seen in cross section C-C the transitional shape can provide a smooth transition between cross section D-D to cross section B-B which can improve insertion and the non-circular shape assists in preventing rotation and migration of the device as described in detail herein. In some embodiments, as shown in FIG. 5, the flat surfaces or less rounded surfaces of the shaft zone of the nail as shown in the cross section C-C and B-B can be positioned on the anterior or posterior portions of the nail to assist in insertion and aid in guiding or predicting the curvature of the nail as described herein. For example, FIGS. 5 and 6 show the one or more flat surface on the anterior portion 100 of the shaft zone of the nail while the posterior portion 200 of the shaft zone of the nail is more rounded.

Figure 6:
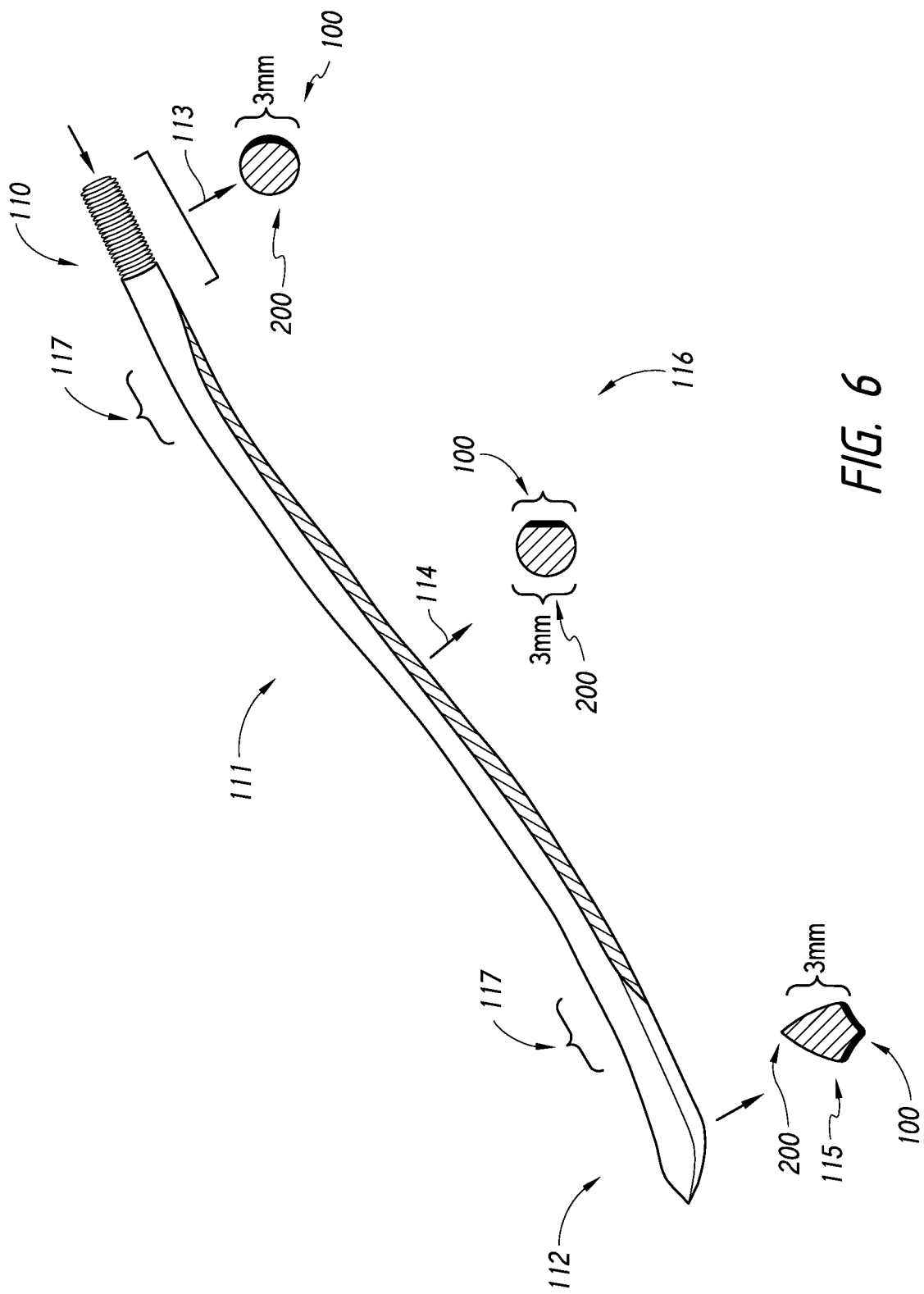
FIG. 6 illustrates an embodiment of a surgical nail with the lateral/medial and posterior/anterior portions of the surgical nail shown.

FIG. 6 illustrates an embodiment of the surgical nail with the lateral 112/medial 110 and posterior 111/anterior 116 portions of the surgical nail more expressly shown. The posterior portion of the nail refers to the portion of the nail directed toward the back side of the body of the patient when the device is implanted. The anterior surface of the nail refers to the portion of the nail directed toward the front side of the body of the patient when the device is implanted. The shaft of the nail can have an anterior and posterior portion that defines the positioning of the nail within the clavicle bone or other small bone, with the medial end (or proximal end) and the lateral end (or distal end) referring to the lateral side and medial side of the clavicle bone or other small bone. FIG. 6 illustrates a nail similar to the nail modeled in FIGS. 2, 3A-G, and 4A-G as it includes varying cross sectional shapes and configurations along the length of the nail device. FIG. 6 includes cross sections 113, 114, 115 and dimensions labeled for an embodiment of the surgical nail. The specific cross sections for each zone are shown. The transitions 117 of the cross section from one portion of the nail to the next can be seen in FIG. 6. This shows an embodiment of how one portion of nail transitions to the next and the associated dimensions and non-circular or circular sections of the cross section. In some embodiments, the nail can have more than one transition 117 or transition zone. For example, the nail can include a transition zone on either end of the shaft (as shown in FIG. 6) and/or the nail can include one or more transition zones within the shaft zone.

As shown in FIG. 6 portions of the nail can include a cross section with at least one flat side. Certain geometries and arrangements of the flat edges can be included to provide an anti-rotational feature of the nail system. For example, the cross section of the distal tip portion, which is also referred to herein as the end zone, can include four flat sides and can have an anterior-posterior length of about 3 mm as shown in FIG. 6. In some embodiments, the anterior-posterior length of the cross section of the distal tip can be between about 2 mm to about 4 mm for surgical nails for small bone surgery including but not limited to clavicle fracture surgery.

The flat sides of the cross section of the distal tip portion can have various sizes. In this embodiment, the two flats on the posterior side of the nail may be larger or longer than the two flats on the anterior side of the nail as shown in cross section 115. Further, as shown in FIG. 6, in some embodiments, a central portion of the shaft proximal to the distal tip, which is also referred to herein as the shaft zone, can have a cross section 114 that can include a 270 degree circular portion that extends over the posterior side of the nail and a flat surface on the anterior side of the nail. This arrangement can provide for an anti-rotational screw with a flat section in the central portion of the screw. A first transition zone with transitional shapes as described further below along its length is positioned between the distal tip portion and central shaft portion. The medial or proximal end of the nail can include a round cross section that can be configured to receive an end cap. A second transition zone with transitional cross sectional shapes (as described further below) along its length can be positioned between the central shaft portion and the proximal most end of the nail with the round cross section as shown in cross section 113. As shown in FIG. 6, the proximal or medial end of the nail can include a circular or round cross section that can be about 3 mm in diameter. In some embodiments, the diameter of the round cross section of the proximal end of the nail can be between about 2 mm to about 4 mm for surgical nails for small bone surgery including but not limited to clavicle fracture surgery. For surgical nails for small bone surgery including but not limited to clavicle fracture surgery, the proximal-distal length of the surgical nail can be between about 100 mm to about 150 mm. Additionally, for small bone surgery for the ulna, the anterior-posterior length of the cross section of the nail can be between about 2 mm to about 8 mm and the proximal-distal length of the surgical nail can be between about 260 mm to about 320 mm.

In some embodiments, the proximal or medial end of the nail can include a threaded screw portion. In some embodiments, the threaded screw portion can be utilized to secure the nail within the bone and/or can be configured to allow complementary fitting with an interior threaded end cap. The threaded end of the nail can have a shaft diameter of about 2.25 mm and an outer screw diameter including the threading portion of about 3 mm.

The various cross-section geometries of the multiple zones of the nail as described herein can include specific round and/or flat geometries at the distal and proximal ends of the nail and varying geometries in between. These various cross sectional geometries can be optimized to improve bone impaction, achieve optimal bone engagement, and reduce rotation within the bone. Zones with circular or rounded cross-sectional areas (substantially oval, circular, smooth, minimally rounded edges not included) result in extensive bone impaction away from the center of the device and toward the periphery of the bone. The bone impaction, while potentially useful to create a snug fit within the bone, can create some problems in certain areas within a small-bone nail. These problems can include: (1) all zones proximal to the rounded zone, unless substantially larger will have reduced bone engagement due to bone impaction created by the more distal rounded zone as it passes through the bone canal first, and (2) despite impacting the bone, the rounded zone is more likely to rotate within the bone as opposed to a zone with at least one flat surface.

In some embodiments, the surgical nail is arranged to allow for enhanced engagement with the bone along the length of the nail and to reduce rotation of the nail. In some embodiments, all zones, with the potential exception of the proximal most zone, advantageously contain at least one flat surface. Additionally, in some embodiments, from the distal end to the proximal end of the nail, all zones should either maintain cross-sectional area or increase in cross section area (with the exception of the proximal most zone). In some embodiments, some rounding of cross-sectional areas can be used moving from the distal end to the proximal end of the nail and this rounding can be achieved by simply rounding flat surfaces away from the center line that runs along the length of the nail. In some embodiments, the largest dimension of all zones can remain constant throughout the nail device shaft, with the exception of the proximal most zone. In some embodiments, all zones of the surgical nail can remain symmetrical to aid in the stability of the device and clarity of orientation during surgery.

In some embodiments, the most proximal zone of the nail can be a fully circular zone in order to facilitate a threaded shaft zone and its connectivity with a threaded end-cap. Additionally, the nail of this embodiment can have an added bone impaction on the proximal end. In some embodiments, the treaded end zone can be used to ease retraction of the device from the bone if needed. In other embodiments, the most proximal end can be made in a non-circular form and with various other end-cap connection designs.

The clavicle bone as illustrated in FIG. 2 has a gentle S-shaped curve that varies from person to person. This S-shaped curve can make it challenging to create a device that adapts to the S-shaped curve of the bone and facilitates insertion into the bone.

The surgical nail as shown in FIGS. 2, 3A-G, 4A-G, and 5 can have a bend that is formed in the nail prior to insertion and/or upon manufacture of the nail device. The pre-bent nail can adapt to the S-shaped curve and facilitate insertion by adding gentle curvature along a specific axis. The axis can be varied depending on the clavicle bone geometry, whether the nail will be inserted into the left or right clavicle, and/or whether the nail will be inserted into the medial or lateral end of the clavicle. The curvature of the nail can be along the z-axis of the nail as shown in FIGS. 1, 2, 3A-G, and 4A-G. The curvature along the z-axis creates a curve that goes into and out of the page. The pre-bend of the nail can have a gentle curvature that includes a gentle C-shaped or S-shaped are to allow for easier passage and control while deploying the nail into the bone. During insertion, the surgeon can turn the C-shaped body to direct the cutting end where desired to ease insertion and advance the nail device into the bone.

The embodiments as illustrated in FIGS. 2, 3A-G, 4A-G, and 5 depicts two areas of gentle curvature. The curvature can be approximately 15%-40% of the radius of curvature of the clavicle in each transition zone. The more distal curvature of the nail allows for easier insertion along the curvature of the clavicle and can be adjusted by the surgeon. In some embodiments, the nail can be bent or curved during insertion or can be pre-bent or shaped during manufacture or by the surgeon prior to insertion. The curvature along the z-axis forms a curved nail that curves into and out of the page mimicking the curvature of the clavicle bone. The curvature can clarify the device orientation for the surgeon. In some embodiments, the curvature can promote bending of the titanium nail along a specific, more predictable axis due to the pre-bend of the nail. Titanium nails might naturally bend within the clavicle and the bending can be preferred to reduce rotation of the device within the bone but unpredictably bending of the nail can lead to unexpected results.

The size and orientation of the nail can vary depending on the desired results and the surgical procedure and bone fracture being treated as described herein. For example, the human medullary canal of the clavicle is highly variable in shape and size, making the determination of appropriate implant size difficult.

In some embodiments, exposure of the fracture site can be achieved with either graduated separate drill bits in the size of the available nails or a proprietary conical screw or awl with marks indicating the sizes of the nails.

End Zone:

The end zone at the distal end or first end of the nail as described above can have a cutting leading end geometry. With small bone surgery and in particular clavicle bone fracture surgery it can be difficult to push medullary bone to the periphery and efficiently advance the nail through the curved bone without penetrating the lateral cortex. The surgical nail as shown in FIGS. 2, 3A-G, 4A-G can have an end-zone designed with: (a) slightly tapered or rounded distal tip within the end-zone that will prevent penetration of the lateral cortex; and (2) at least one flat surface with sharp edges that meet at the tapered/rounded tip to facilitate penetration, improved surgeon control of the nail during advancement, and increase impaction of bone. In some embodiments, the slightly tapered or rounded distal tip can be only the final distal millimeter of end-zone along the length of the nail. In some embodiments, the end-zone of the nail can include two flat surfaces. In some embodiments, the end-zone of the nail can have two or more flat surfaces. FIG. 5, FIG. 7, and FIGS. 9A-B illustrate the flat surfaces with hatch marks on the nail.

Figure 7:
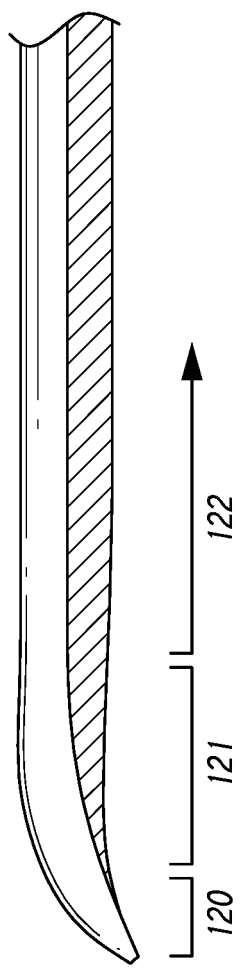
FIG. 7 illustrates an embodiment of a small bone surgical nail system with multiple zones as shown with three distinct zones: the end zone; the transition zone; and the shaft zone.

As shown in FIG. 7 and FIG. 8, the end zone 120 encompasses the tip portion of the device. The tip is the first portion of the device that enters the bone in small bone surgery. In some embodiments, to repair a clavicle fracture the nail may enter the fractured clavicle from the medial end of the clavicle at the sternum and be advanced through the bone toward the lateral end of the clavicle. In such embodiments, the tip portion of the device is referred to as the distal tip. However, the nail may enter the fractured clavicle from the lateral end of the clavicle at the shoulder and in such embodiments, the orientation, geometry, and components described herein would be reversed. Since the nail system can enter the bone in various orientations and/or entry points, the ends of the nail system can be described herein as having a leading end (an end that passes through the bone first) and a trailing end (an end that is passes through the bone after the leading end). The terminating end or leading end of the tip of the end zone is always sharp (non-dull) to simplify precise entry into the small bone. For small bones in particular, the entry geometry (tip, cross section, and curvature) can be important to successful and simple entry. Various end zone designs can be used. The cross section of the end zone can be non-circular. FIG. 8 illustrates cross-sections of the end zone of the device that can be used. The end zone design can simplify entry into the bone, as well as bone fragments that resulted from a fracture, and setup efficient placement of the rest of the device including the transition and shaft zones. The end zone can include a cutting geometry that creates a path through the medullary canal of the bone.

Figure 9A:
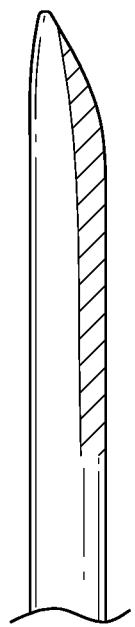
FIGS. 9A-B illustrate embodiments of designs of the surgical nail end zone with limited or no curvature and a distal end that is not dull.
Figure 9B:
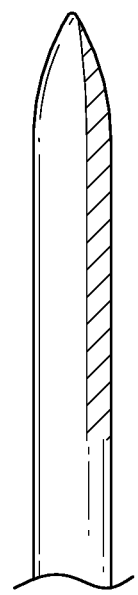

The end zone can include a particular curvature, excluding a dull tip. The angle or curvature of the end zone can ease the insertion and/or extraction of the device. While the end zone can be curved or angled, the cross section of the end zone can remain the same throughout the zone. In some embodiments, only one side of the end zone is curved while at least one side is flat. In yet other embodiments, the end zone can be a non-curved or straight zone. FIGS. 9A-B illustrate embodiments of designs with limited or no curvature and an end zone with a tip that is not dull. In some embodiments, the end zone can have two or more sides that are curved, for example in a bow structure along a specific angle. This end zone design can allow for more efficient advancement and quick placement in the clavicle or other small bone. FIG. 9A illustrates an embodiment of an end zone with one flat edge and one curved or angled edge. FIG. 9B illustrates an embodiment of an end zone with both edges curved or angled toward the tip. The end zone can be sectionalized to allow for bending around the curved edges within the bone. The sectionalized end zone can include an end zone that is segmented and each segment can move relative to one another to ease bending around the curved edges within the bone.

FIGS. 9A and 9B show the contrast between a single flat edge with added sharpness at the tip for easier insertion and control versus a symmetrical curved tip.

FIG. 9C shows another embodiment of a surgical nail system. FIG. 9C illustrates the cross-sectional areas of the end zone 120, a transition zone 121, and a shaft zone 122 that show the difference in cross-sectional area between the zones and how the nail device transitions form one zone to the next. The end zone 120 is shown with the sharp cutting geometry and without a large radius of curvature. The shaft zone 122 can have flattened sides that can improve rotational stability as described in more detail herein. Further, FIG. 9C illustrates the use of a locking end cap 123 as well as blocking screws 124 and deflecting screws 125. The blocking screw and deflecting screw can be used to prevent migration of the nail out of the bone as described herein. The blocking screw 124 can be used to physically prevent the nail from backing out. The deflecting screw 125 can be used to keep the nail positioned away from the insertion site.

Transitional Zones:

In some embodiments, the nail device can include a distal end or leading first end with a distinct and detailed geometry (e.g., non-rounded cross section) and the geometry can change (e.g., cross section can increase) along the length of the nail to form a very different geometry (e.g., round cross section) at the most proximal or trailing end. To achieve a smooth transition between the geometries of the distal or leading end and proximal or trailing end, one or more transition zones can be present in the surgical nail design.

For small bone surgeries, precision and control are paramount. In addition, the bone impaction and healing around the nail has greater impacts on the clinical outcome, including healing of the fracture site, usability of the bone post surgery, simplicity of nail extraction, and the pain levels the patient might experience while the nail remains implanted within the patient's body. Hence, any geometric changes within the nail (e.g., cross-sectional areas, curvature) could complicate the procedure, healing, stability, or device retraction. Therefore, a transition zone can be utilized as an extremely effective intermediate zone positioned in between zones of the nail device to provide for preferred and predictable behavior during and after surgery. The transition zone can contain different design features and geometries than those present in the end zone and shaft zone. The transition zone can provide for a gradual change between two different zones of the nail device. The gradual change between the zones can be a minimum length of 1 mm and an optimal length range of 1 mm-30 mm (although no maximum limit on transition zone length should be applied). In some embodiments, the gradual change between the zones can be a minimum length of less than 1 mm. The gradual change of geometry can facilitate entry (surgeon control) of the nail, maintain uniformity of bone impaction around the nail (improved rotational stability), and facilitate extraction of the nail. For example, as the nail enters the bone, the end zone (tip) first creates a tunnel or opening in the bone. If the nail's cross sectional geometry is rapidly increased, bone will push on the end zone of the thicker cross sectional geometry and prevent smooth insertion. In the opposite example, if the nail's cross sectional geometry is rapidly reduced or changed in any axis direction (e.g., x, y, or z-axis), the more proximal or trailing portion of nail may contain space around it where the dimensions are smaller than the end zone. This space is extremely undesirable because it decreases rotational stability of the nail, leads to less predictable healing, and complicated extraction of the nail. With gentle and strategic transitions zones that are uniquely designed based on the geometry of the adjacent zone(s), bone contact is maintained and outward pressure on the bone is increased at a slower rate—achieving controllable insertion of the nail and consistent bone impaction around the nail. Additionally, in some embodiments, the geometry of the transition zone can have no point along the length of the nail that is more rounded or circular than the immediate most proximal or trailing zone, with the exception of the transition to the proximal most or trailing most zone. This feature can be critical to maintain uniformity of bone impaction. In some embodiments, when rounding of cross-sectional areas occurs from distal to proximal end of the nail, the transition zone can be achieved by simply rounding flat surfaces away from the center line of the nail. The center line of the nail can be defined by an imaginary line down the center of the nail and running through the center of the nail along its length. In some embodiments, restricting other forms of transition assists with entry, removal, and uniformity of bone impaction. In some embodiments, the transition zones can adopt the principles of the cross sectional areas and lengths of each zone as shown in FIG. 6.

Figure 10:
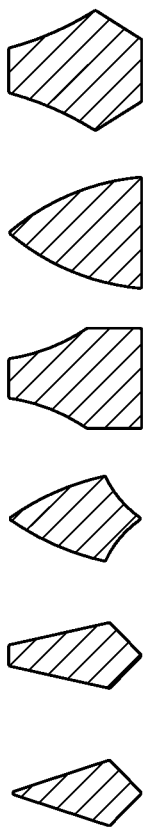
FIG. 10 illustrates embodiments of the cross sectional areas of the transition zone.

One advantageous aspect of the transition zone in some embodiments is that it transitions the cross-sectional area of the proximal or trailing end of the end zone into the distal or leading end of the shaft zone. The characteristics that can impact the efficiency of small bone surgery within this zone are the length, curvature, shape, and rate of change of the cross-sectional area. The cross sectional area of the transitional zone can be greater than or equal to the cross sectional area of the end zone. FIG. 10 illustrates embodiments of the cross sectional areas of the transitional zone.

Another advantageous aspect of the transition zone in some embodiments is the transition of the shape of the cross sectional area within the end zone (distal or leading side of the transition zone) to a different design shape within the shaft zone (proximal or trailing side of the transition zone). As shown in FIGS. 11A-B, the transition from the sharp to flat edge cross-section of the small bone surgical nail device can be advantageous for placement of the device within the bone. For example, as shown in FIG. 11A, the device can transition from a sharp edge to a flat edge cross-section using an intermediate cross-section that gradually expands to flat edges on all sides of the device by having portions with some flat edges on some of the sides as it moves from the distal or leading end to the proximal or trailing end of the transition zone. FIG. 11B illustrates an embodiment comprising a round or more circular cross section for the transitional zone. In some embodiments, the round cross section of the transition zone can cause the transition zone of the device to push the cancellous bone to the periphery and thereby not allowing engagement of the shaft zone. Therefore, in some embodiments, there is no round cross-section in the transitional zone.

Shaft Zone(s):

In some embodiments, the surgical nail can have a shaft zone with a nail body having a cross section with at least one flat edge on the surface of the nail. Surgical nails for small bone surgery and clavicle fracture surgery can have challenges related to rotational stability of the device. Achieving rotational stability of the device can be very difficult to attain, for example, because of the small diameter of the bone and/or implants. Some circular or primarily rounded implants can provide little rotational friction to aid with rotational stability. The surgical nail device as illustrated in embodiments in FIGS. 2, 3A-G, 4A-G and other embodiments disclosed here can include, except at the most proximal or most trailing end of the shaft zone, a shaft body with a cross section with at least one flat side or edge on the nail body to aid in the rotational stability of the nail device. Additionally, the surgical nail can maintain continuity of design between zones (end-zone to shaft-zone and/or shaft-zone to shaft-zone). In some embodiments, the end zone shape can be substantially maintained and the flat surfaces are not retracted but instead expanded into the first shaft zone.

Figure 12A:
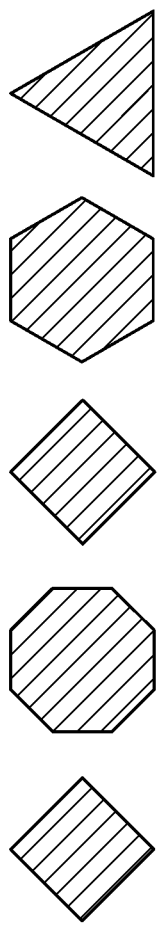
FIGS. 12A-C illustrate embodiments of cross-sectional shapes for the shaft zone.
Figure 12B:
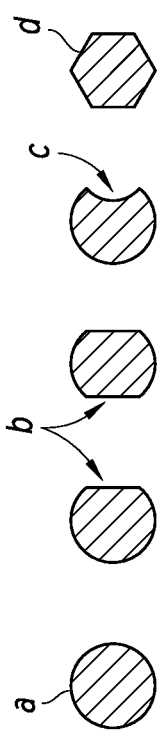
Figure 12C:
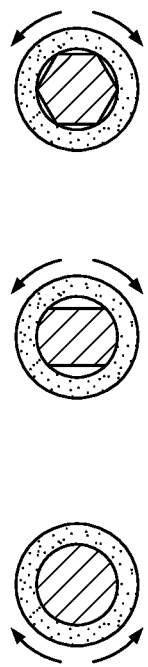
Figure 13:
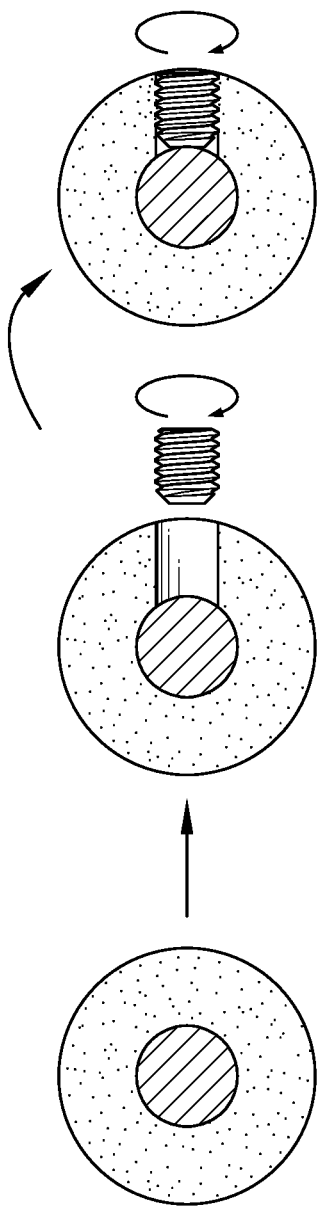
FIG. 13 illustrates an embodiment of the surgical nail system device adapted to receive at least one locking screw.

The shaft zone encompasses the zone (or zones) on the proximal or trailing end of the device, and may comprise the entire length of the shaft proximal to or trailing the end zone and the transition zone. The distal or leading end of the shaft zone begins at the proximal or trailing end of the transition zone as shown in FIG. 13. The shaft zone can be the longest zone and can be designed with specific cross-section, curvature, and proximal geometry to improve surgical outcomes. FIGS. 12A-C illustrate possible cross-sectional shapes for the shaft zone area. Various curvature lengths and angles are envisioned to maximize strength during bending while also aiding insertion of the device into small bone spaces. The cross sectional area of the shaft zone can be greater than or equal to the cross sectional area of the transitional zone. As shown in FIG. 12A, the shaft zone can comprise a flat geometry or include flat ends to prevent rotation of the bone around the implant.

FIG. 12B shows alternate cross-sectional geometries for the shaft zone. FIG. 12B illustrates cross section (a) with a standard cylindrical shape, cross sections (b) with any flat edges, cross section (c) with any convex/concave edges, and cross section (d) with any new cross sectional shape. As shown in FIG. 12C, the flat edges or convex/concave edge of the cross sectional shape can be used to improve the rotational stability of the device. The flat or convex/concave edge of the cross sectional shape can compact the surrounding bone improving rotational stability and/or engagement of the shaft zone to the bone. In some embodiments, the design elements of the end zone, transition zone, and/or shaft zone can be mixed and matched with one another. The order is interchangeable to create a broad diversity of available nail designs, with the principles of design described herein to provide the added functionality and control desired to improve clinical outcomes.

Locking Screw:

Nails may back out, migrate, become damaged, or cause discomfort over time, requiring a secondary procedure to remove them. To reduce movement of the nail an optional blocking device such as, for example, a screw can be used. In some embodiments, a unicortical blocking screw, similar to the unicortical screw illustrated in FIG. 13, can be placed just lateral/peripheral to the entry hole on the sternal side to prevent the body of the nail from backing out of the same hole. Given the complication of backing out of small nails a simple blocking screw can be used as an alternative to an end cap if an end-cap is not possible or based on a preference of the surgeon.

The device can be used with one or more locking screws that can engage the small bone surgical nail device and secure the device within the bone. Various forms of a locking screw(s) can be utilized to help hold the device in place. In some embodiments, the nail device may be modified to receive the locking screw(s). The locking screws can, for example, engage the nail device within the shaft zone. As shown in FIG. 13, the device may be adapted to receive at least one locking screw, for example, in a plane perpendicular to the device, to lock the device in place. For example, in some embodiments, as illustrated in FIG. 13, (a) the nail is present within the bone, (b) a unicortical hole can be drilled in the bone and (c) a unicortical locking screw is placed in the hole to secure the nail device in place within the bone.

Traditional locking screw designs and mechanisms may also be applied. In some embodiments, the nail device can also contain an indentation (threaded or not) to receive the locking screw. In some embodiments, the shaft zone of the device can also contain a tunnel/hole for each locking screw that allows the associated locking screw to pass through the entire device shaft.

In some embodiments, a locking screw 30 can be used in coordination with an end cap 20 as shown in FIG. 2, FIGS. 3A-G, and FIGS. 4A-G. The locking screw can be used to secure the surgical nail system in place and prevent rotation and movement of the nail system. The locking screw 30 can be inserted into a tab portion of the end cap. The tab portion can include a proximal or trailing end extending portion extending away from the end cap and an end plate portion that engages an outer surface of the bone. The proximal or trailing extending portion of the tab can have an aperture that allows the screw body to pass through. The aperture is sized to be bigger than the screw body to allow the screw body to pass through and to be smaller than the screw head to prevent the head of the screw from passing through.

Figure 14A:
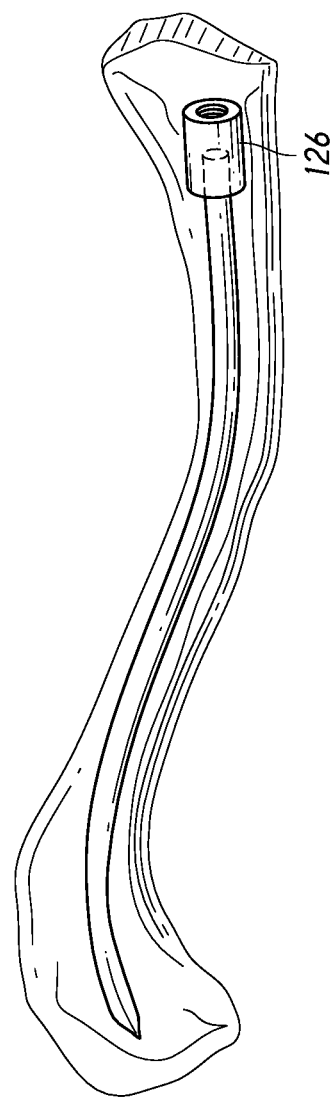
FIG. 14A illustrates an embodiment of the end cap secured to the end of the nail and the entire unit advanced into the bone.
Figure 16B:
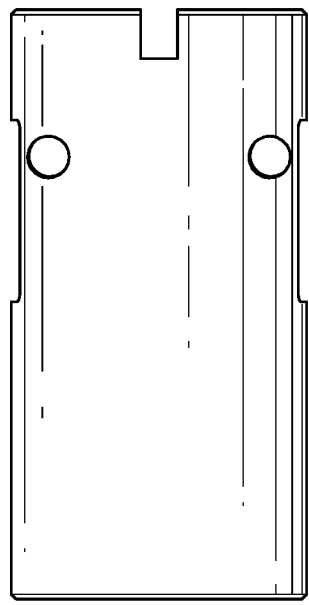
FIG. 16A-D illustrates views of an embodiment of the end cap design with locking wings.
Figure 16D:
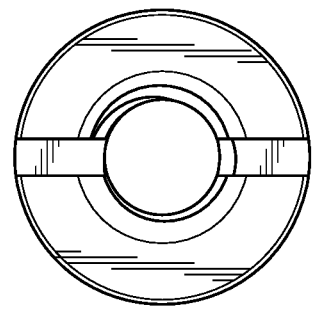
Figure 16A:
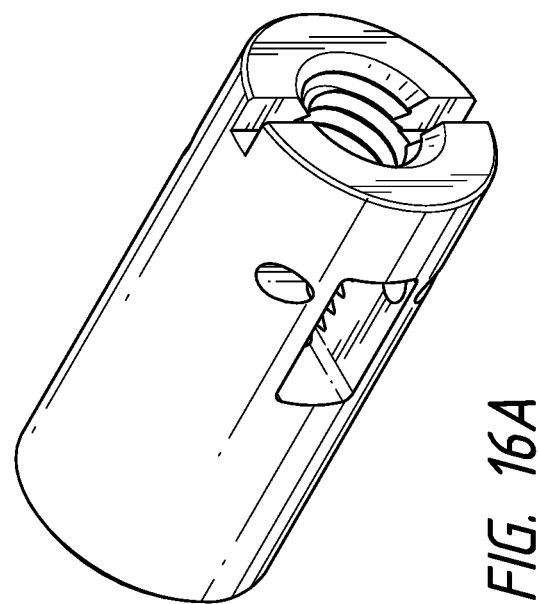
Figure 16C:
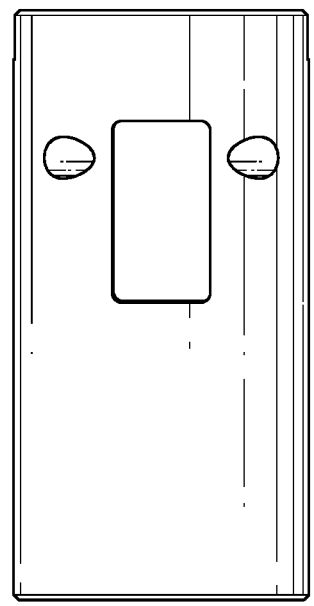

End Cap:

In some embodiments, the surgical system can include a separate end cap. The end-cap can be added to the device head (typically the proximal or trailing end), opposite from the "end zone." In yet other embodiments, if the end cap be used on the device tail or the "end zone." The surgical nails can back out, migrate, become damaged, or cause discomfort over time, requiring a secondary procedure to remove them. The surgical nail can utilize an end cap that caps the end of the nail. The end cap can be a tabbed end cap that utilizes a second screw to keep it in place (e.g., via tabbed hole as described above), the body of the end cap itself may screw into the surrounding bone, and/or the end cap can have locking features to secure into the surrounding bone. The end cap can be tapped into the bone around the nail by the surgeon or crimped on the nail by the surgeon. The end cap can be designed to remain at least partially submerged within the bone. The end cap can be designed to remain fully submerged within the bone. A submerged end cap can include a shape and/or outer surface designed to keep the device comfortably submerged within the bone. In some embodiments, the end cap can be a partially submerged end cap. The device with a partially submerged end cap may also contain end cap geometries to allow for a portion of the end cap to be submerged in bone while the remaining portion is easily accessible on the outside of the bone. In some embodiments, the outside surface of the end cap can be or have a graduated cylinder shape, textured/rough surface to catch onto bone, tunnels or divots to catch bone, single or dual flat surface to catch bone, and/or graduate cylinder such that largest diameter is at the center of the end-cap (graduates up in size and then back down so the end of the cap is more easily submerged or does not stick out). As shown in FIG. 14A, the end cap 126 may be secured to the end of the nail and the entire unit advanced into the bone.

In some embodiments, the end cap system can be manufactured as an attachment to, or connected with, the small bone nail device. Any individual end cap design part or feature disclosed herein can be independently designed into the nail device directly and manufactured simultaneously.

In some embodiments, the end cap 126 can be configured to secure to a proximal or trailing end of nail that is threaded. In some embodiments, a surgeon can cut the nail to the desired length or a surgical kit can be provided that includes nails of multiple sizes. The internal diameter of the distal or leading end of the end cap can be threaded to engage the threaded proximal or trailing end of the nail.

As shown in FIG. 14B, the end cap 126 can include an extraction end cap that has a screw pitch 129 for later extraction. The end cap can be crimped or pressure welded at end 130 to the nail 128 in some embodiments, rather than being threaded into the proximal or trailing end of the nail. The crimping or pressure on the distal or leading end 130 of the end cap cold welds the nail 128 to the end cap 126 while allowing for screw extraction.

As shown in FIG. 14C, the end cap can allow for extraction by a screw-in attachment 127.

FIG. 14D illustrates alternate cross sectional geometries for the end cap. The cross sectional geometries can aid in crimping and rotational stability.

The end-cap is designed to limit movement of the device and ease extraction after healing. The end-cap can include a cold welding design. The cold welding can be a material similar to the device to allow for cold welding and reduce galvanic effects. The end cap can have a crimping design that includes a hollow and/or divot design to allow crimping onto the device. The end cap can include a hollow or donut design that is adapted to receive the device, potentially with screw threads or shaped to receive the device head. The hollow or donut design can include an inner surface geometry adapted to work with the device shaft design to facilitate placement and rotation by the surgeon. The hollow or donut design can include a threaded inside diameter of the end cap that increases friction with the device shaft to increase rotational stability. The design can also include a cross-sectional modification and the inside or outside diameter of the end-cap can be various geometries to increase rotational control and stability. For example, the end cap can include "wings" or protrusions radially outward that increase rotational stability. Yet another example, the end cap can include spikes or other outward protrusion that enter the bone as the end cap is placed over the nail.

In some embodiments, the end cap can be made of more than one part. For example, a first part can contain a cylindrical shaped end cap with holes or apertures on the outer surface designed to mate with the second part. The second part could be a part designed to be place inside or outside of the first part and have protrusion that enter the apertures of the first part. Together, the two part end cap effectively holds the nail in place to prevent migration. In some embodiments, the second part of the end cap is designed to mate with the first part of the end cap, and any type of geometrical shape, or combination thereof, usable for of either part of the end cap. In some embodiments, the second part is pushed into the first part to snap lock the end cap system in place. In yet other embodiments, the second part must be rotated to lock the end cap system in place. For example, the snapping or rotating can push protrusions or wings outward or can contain mating mechanism with the first part to lock the mechanism in place.

In some embodiments, the end cap system contacts the nail upon insertion. Yet in other embodiments, no such contact is required.

Figure 17:
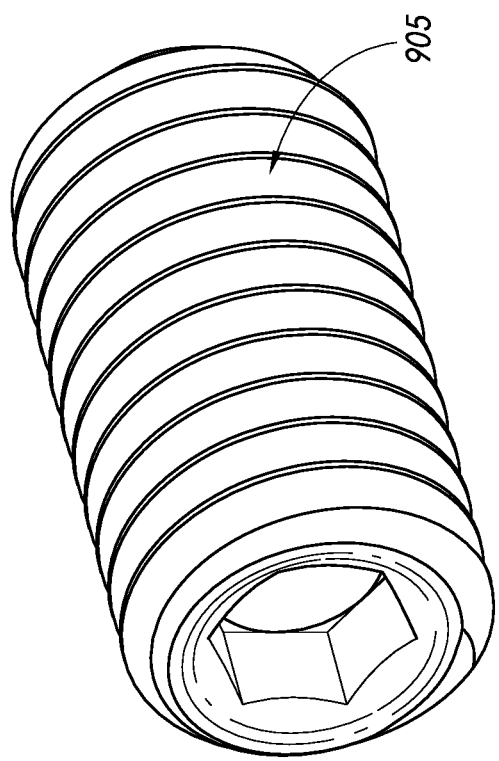
FIG. 17 illustrates an embodiment of the screw for inserting into the end cap design with locking wings.
Figure 19B:
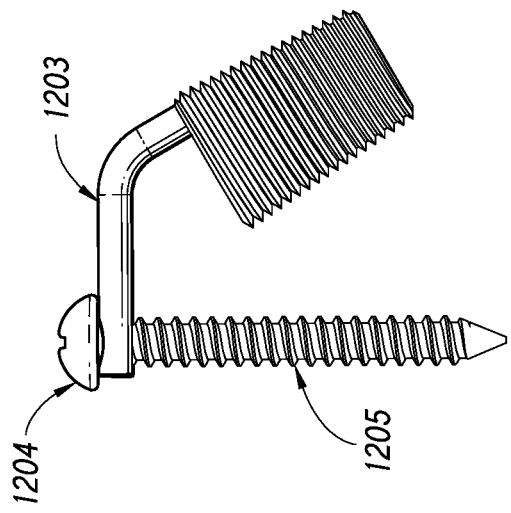
FIG. 19 illustrates views of an embodiment of the end cap design with a tab and screw end cap locking system.
Figure 19D:
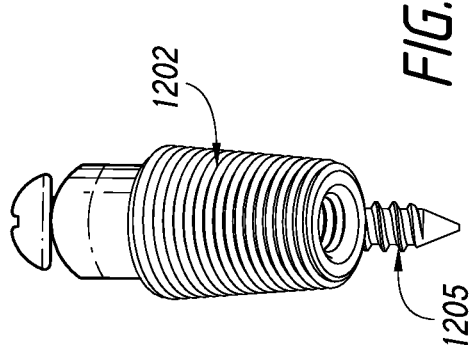
Figure 19A:
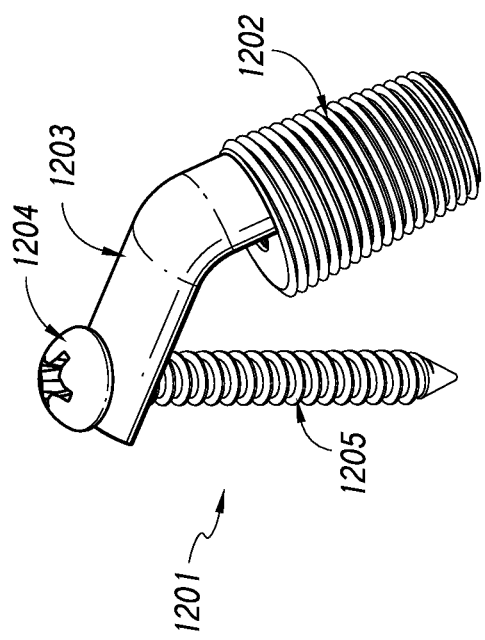
Figure 19C:
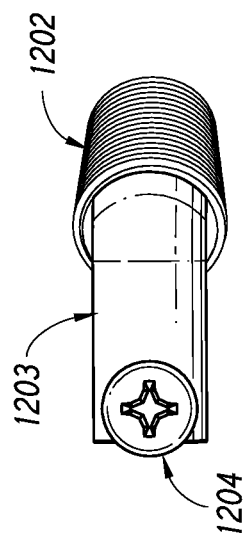

In some embodiments, the end cap can include a locking feature that secures the end cap and nail system into the bone. The end cap can include a winged locking system as illustrated in FIGS. 1, 15A-D, and 16A-D. FIGS. 15A-D illustrate a winged end cap 900 cylindrical in shape and an interior threaded channel 901 running along the length of the cylindrical end cap. The end cap can have a distal or leading end 910 and proximal or trailing end 920. In some embodiments, the distal or leading end 910 can be threaded and configured to attach to the proximal or trailing end of the nail. In some embodiments, a portion or all of the outer surface of the end cap 900 is threaded to be rotated into the bone to increase stability. In some embodiments, the general shape of the end cap 900 is cylindrical, yet in other embodiments, it can be conical, oval, partially rounded, entirely not rounded, or some combination of each. In some embodiments, the proximal or trailing end 920 of the end cap can incorporate the winged locking system. In some embodiments, the proximal or trailing end 920 can be used to receiving an extractor or for attaching external devices to the nail. As shown in FIGS. 15A-D, the end cap includes two wings 902 that can protrude from windows 903 on the surface of the cylinder of the end cap. The wings 902 can move relative to the cylindrical surface of the end cap through a hinge mechanism. In some embodiments, the hinge mechanism can include a pin 904 as shown in FIGS. 15A-D. The wing can have at least two positions. The wing can have a retracted position and an extended position. In the retracted position, the wing can be substantially flush with the outside surface of the cylindrical end cap. In the extending position, at least a portion of the wing 902 protrudes radially outward from the outside surface of the cylindrical end cap as shown in FIGS. 15A-D. The protruding configuration of the wing 902 can increase rotational stability. In some embodiments, the winged locking end cap can utilize a locking screw 905 that can be inserted into at least a portion of the interior threaded channel 901. FIG. 17 illustrates an embodiment of the locking screw 905 used to move the winged end cap into the extended position. As illustrated in FIGS. 15A-D, the locking screw 905 can be inserted into the proximal or trailing end of the end cap. After insertion of the nail and end cap design into the bone, the surgical nail system can be secured in place in the bone by placing the wings 902 in the extended position. In some embodiments, the wings 902 can be extended by inserting the locking screw 905 into the proximal or trailing end of the interior treaded channel 901. As the locking screw 905 passes through the channel 901, the wings are pushed into an extended position protruding from the outer surface of the cylinder.

In some embodiments, only one wing can be used. In other embodiments, two or more wings can be used. In some embodiments, the wings can be connected to the screw or part 905 that is inserted into the part that surrounds the nail 920/900. In some embodiments, the wings can be designed as spikes, cross screws, nails, rounded or domed protrusions, ledges, pyramids, or equivalent mechanism understood by those in art. In small bone surgery, each additional mechanism that prevents migration is a positive. However, the level of attachment to the bone must also be reversible to a degree to allow for retraction of the device if necessary. In some embodiments, the wings can be closer to the nail to accommodate limited bone between the edge of the bone and the nail. Yet in other embodiments, the wings can be placed further away from the nail to make it easier for the surgeon to activate the wings (protrude them out) as well as extract the nail by easier removal of the end cap.

In some embodiments, the hinge mechanism does not utilize a separate pin component but instead the movement of the wing can utilize the flexibility of the material used for the end cap. For example, in some embodiments, the wing can be a tab wing which is a cut out portions of the metal of the cylinder. The cut out tab wings can be cut on three sides and hinged to the cylinder on the fourth side of the rectangular wing. The cut out wing can be moved to the extended position by insertion of a locking screw or other device that can move the cut out portion of the wing outward rotating around the connected hinged side so that it protrudes radially outward from the outside surface of the cylinder similar to the extended position shown in FIGS. 15A-D. In some embodiments, the wings are strategically placed thickened portions of the end cap wall. In some embodiments, the thickened portion of the end cap wall is on the inner surface of the cap such that the wings can be protruded into the surrounding bone by simply applying pressure on the inner surface of the end cap (e.g., with a screw or nail). In some embodiments, many layers, levels, or sizes of wings or protrusions can be included to make the end cap more flexible for each surgery.

FIG. 16A-D illustrates several views of an embodiment of the cylindrical winged end cap illustrated in FIGS. 15A-D without the wings, hinge, and locking screw included. FIG. 17 illustrates an embodiment of the locking screw 905 used with the winged end cap and inserted into the interior channel of the end cap to move the wings into the extended position.

FIG. 18A-C illustrates several embodiments of the end cap designs for a clavicle nail surgical system. In some embodiments, the end cap can be a cylindrical (hollow) cap that has screw threading on the inside as shown in the top embodiment of FIG. 18A-C. The screw threading on the inside can be utilized to connect to and engage with the threads on the proximal or trialing end of the clavicle nail. In some embodiments, the end cap can have a screw threading on the outside surface of the end cap to allow the end cap to sit snugly in the bone and help anchor the surgical nail system into the bone. In some embodiments, the end cap 131 can include a tab with a screw hole as shown in the embodiment of FIG. 18C. In some embodiments, a screw 132 can be inserted into the tab of the end cap 131 to prevent migration of the nail system. In some embodiments, the end cap can have a conical, square, or rectangular cross-sectional shape. In some embodiments, the end cap can be asymmetrical in shape or include multiple cross sections shapes. In some embodiments, the end cap can include pre-fabricated cut outs or divots to allow the surgeon to more easily cut a portion of it during surgery to adjust to provide more optimal dimensions for each given surgery. A marker or divot on the end cap can be used to provide a short-hand measurement for the surgeon to see how deep the end cap is within the bone or how close the nail is to the surface of the bone. The variety of outer shapes can provide stability by screwing into the bone and/or wedging into the bone. In some embodiments, the end cap can have various outer shapes to provide stability by screwing or wedging into the bone. As shown in FIG. 18A, the end cap can have an outer shape that is (a) smooth, (b) spiral or treaded, or (c) angular.

The dual thread option of the end cap design as shown in the embodiment of FIG. 18B can have an interior threading with a positive thread and a negative thread. The positive thread and the negative thread have threading rotating in opposite directions from each other. For example, in some embodiments, the positive thread can be used to attach the proximal or trailing end of the nail (with a complementary positive thread) to the interior of the end cap and the negative thread can be used to attach an extraction device or screw (with a complementary negative thread) inside the end cap. In some embodiments, the screw inside the negative thread end of the end cap can be used to keep bony ingrowth out of the negative thread end and maintain that end for receiving the extraction device when extraction of the end cap and/or surgical nail system is required. In some embodiments, the side connecting to the nail end can have a negative thread and the side connecting to the extraction device or screw can have a positive end and the proximal or trailing nail end and the extraction device and screw will have the complementary threading. In some embodiments, the side of the end cap for connecting to the nail and the side of the end cap for connecting to the extraction device or screw can both have positive or both have negative threading and the extraction device and screw will have the complementary threading.

In some embodiments, the nail and/or end cap can have single or graduated pre-fabricated markings to aid the surgical procedure. The markings can help indicate how much of the nail has been inserted. In some embodiments, the markings can assist the surgeon to know the best place to cut the nail to the desired length. In some embodiments, the markings on the nail can have similar or corresponding marks on the end cap to assist the best and quickest placement of the end cap by the surgeon. In some embodiments, the markings can be divots or protrusions that physically interact with the end cap to notify the surgeon of how far the nail or end cap has been inserted.

The tab end cap design as shown in the embodiment of FIG. 18C is similar to the end cap design shown in FIG. 2, FIGS. 3A-G, and FIGS. 4A-G. The tab end cap design 131 includes a flange on one side of the end cap that includes an aperture configured to receive a screw 132 or other securing device. The tab end cap can also have an interior treaded portion that can screw onto a complementary threaded portion on the proximal or trailing end of the surgical nail. For example, the end cap can be screwed and locked to the proximal or trailing end of the nail and a bicortical screw 132 can be inserted through the aperture in the flange to prevent migration.

In some embodiments, the end cap can be a tabbed end cap with a locking screw 1201 as illustrated in FIG. 19. In some embodiments, a separate locking screw can be used in combination with the end cap to further prevent the nail system from backing out of the bone as described previously. The end cap can have a screw to keep it in place (e.g., via tabbed hole), or the body of the end cap itself may screw into the surrounding bone. The embodiment depicted in FIG. 19 can be configured to secure to a proximal or trailing end of the nail that is threaded. In some embodiments, a surgeon can cut the nail to the desired length or a surgical kit can be provided that includes nails of multiple sizes. As shown in FIG. 19, the outer diameter 1202 of end-cap is also threaded to dig into the surrounding bony structure when inserted into the bone. In some embodiments, the outer diameter 1202 of the end-cap gradually can increase in diameter along the length of the end cap from the distal or leading end to the proximal or trailing end to improve the connectivity of the end cap to the bone. In some embodiments, the tab 1203 can extend from the end cap and can include a screw hole 1204 to receive the locking screw 1205 as shown in FIG. 19. In some embodiments, the tab 1203 can be bendable or removable by a surgeon or other user. The locking screw 1205 can be inserted through the screw hole 1204 to provide a locking mechanism and secure the surgical nail system to the bone.

Figure 20:
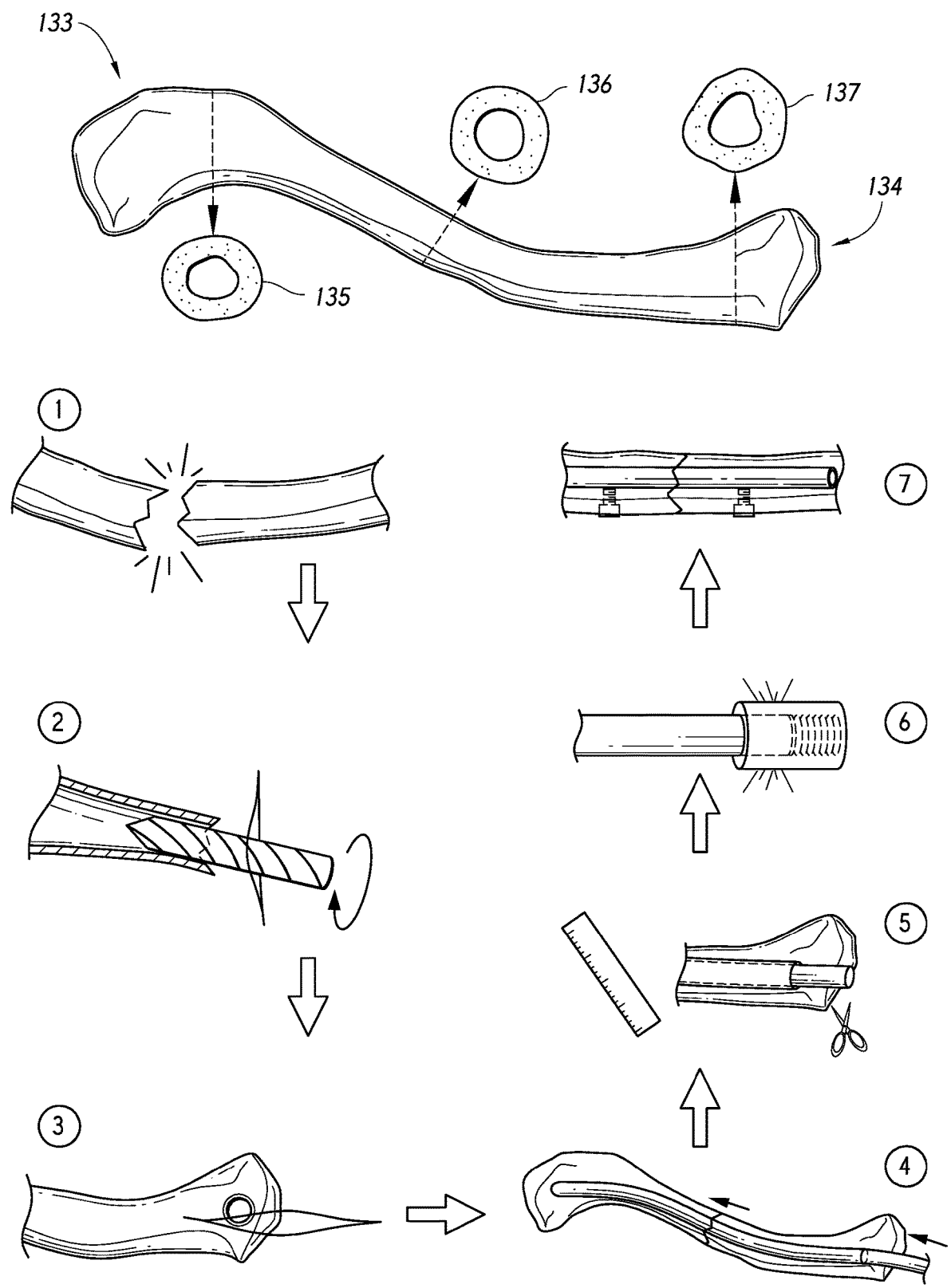
FIG. 20 illustrates a clavicle fracture procedure with an embodiment of the surgical nail system.

The small bone surgical nail system can be used in various small bone procedures. For example, FIG. 20 illustrates a clavicle fracture procedure. FIG. 20 illustrates a clavicle bone with the acromial articulation or shoulder end 133 of the clavicle and the sternal articulation or chest end 134 of the clavicle. Cross section 135 illustrates the lateral cross section which is elliptical, cross section 136 illustrates the central cross section which is round, and cross section 137 illustrates the medial cross section which is round. The clavicle fracture procedure is illustrated with reference to steps 1 through 7 of FIG. 20. Step 1 illustrates the midshaft (diaphyseal) clavicle fracture. Step 2 illustrates the incision over the fracture site and sizing of clavicular diaphysis. Step 3 illustrates a medial incision and opening at the sternal articulation. In some embodiments, the opening can be done with a drill or awl. Step 4 illustrates advancement of the nail through the entire clavicle. Once the nail is advanced through the clavicle, the fracture is aligned by the nail. Step 5 illustrates that the nail can be measured or sized to the desired length and/or cut to be flush with the bone. Step 6 illustrates the placement of an optional end cap that can be inserted on the sternal or trailing end of the nail. The end cap can be crimped to fix the end cap to the nail as described previously or any other end cap configuration or technique described herein can be used. Step 7 illustrates the optional placement of one or more locking screws. The locking screw can be placed in a central region of the bone and nail as shown in FIG. 20 and/or any other placement of locking screws described herein can be used.

The embodiments of FIG. 20 as well as the embodiments described with reference to other Figures describe the insertion of the nail system from a sternal or medial end of the clavicle and advancing the nail through the bone toward a shoulder or lateral end of the clavicle. However, depending on the bone or fracture being repaired, the nail can be entered through various positions within the body. For example, to repair a clavicle fracture, it is understood that the nail may enter the fractured clavicle from either the distal/lateral end of the clavicle at the shoulder or the proximal/medial end of the clavicle at the sternum. Therefore, in embodiments where the nail is entered from the lateral or shoulder end of the clavicle, the nail geometry described herein can be reversed from the proximal to distal end of the nail system from that described with reference to FIG. 20 as well as other figures herein. Therefore, in such embodiments, the components and zones described on the proximal end of the nail would be on the distal end of the nail and the components and zones described on the distal end of the nail would be on the proximal end of the nail. Additionally, in such embodiments, the end cap and lock screw can be positioned at the lateral end of the surgical nail once inserted into clavicle. Regardless of the entry point of the nail, the nail system is advanced through the bone from one end toward the other end. Therefore, as used herein the description of the components of the nail system can be referred to as having a leading end (an end that passes through the bone first) and a trailing end (an end that is passes through the bone after the leading end).

As described herein, the reference to the positioning of the nail as anterior, posterior, medial, or lateral describes one orientation of the nail. However, the positioning of the nail with respect to a patient's body can change or flip depending on the entry point of the nail as well as the bone the nail is used to repair. The nail system described herein can allow for multiple entry points for entry and/or removal of the device as well as use in multiple small bones.

Although some details, geometries, and configurations of the device and system are described herein with respect to clavicle fracture surgery, the device can also be used in other types of small bone surgeries. For example, the device and systems described herein can be used for ulna surgery.

All of the features disclosed in this specification (including any accompanying exhibits, claims, abstract and drawings), and/or all of the steps of any method or process so disclosed, may be combined in any combination, except combinations where at least some of such features and/or steps are mutually exclusive. The disclosure is not restricted to the details of any foregoing embodiments. The disclosure extends to any novel one, or any novel combination, of the features disclosed in this specification (including any accompanying claims, abstract and drawings), or to any novel one, or any novel combination, of the steps of any method or process so disclosed.

Various modifications to the implementations described in this disclosure may be readily apparent to those skilled in the art, and the generic principles defined herein may be applied to other implementations without departing from the spirit or scope of this disclosure. Thus, the disclosure is not intended to be limited to the implementations shown herein, but is to be accorded the widest scope consistent with the principles and features disclosed herein. Certain embodiments of the disclosure are encompassed in the claim set listed below or presented in the future.

What is claimed is:

1. A clavicle nail fixation system, the system comprising:
   a nail sized for positioning within a clavicle bone, the nail comprising an elongate shaft having a proximal end and a distal end, the nail comprising multiple zones along its length having various cross-sectional geometries; and
   wherein:
      the nail has a first cross-section with a plurality of flat surfaces and a second cross-section with a single flat surface, wherein the second cross section is proximal to the first cross-section;
      the nail comprises an end zone at its distal end having a first cross-sectional shape and a shaft zone proximal to the end zone having a second cross-sectional shape, wherein the first cross-sectional shape is different from the second cross-sectional shape;

the nail comprises a transition zone between the end zone and the shaft zone;

the transition zone has a third cross-sectional shape that is different from the first cross-sectional shape and the second cross-sectional shape;

the shaft zone has a cross sectional area greater than or equal to a cross sectional area of the transition zone and the cross sectional area of the transition zone is greater than or equal to a cross sectional area of the end zone; and the transition zone has a length of at least 1 mm.

2. The system of claim 1, wherein at least the end zone has a non-circular cross section.

3. The system of claim 1, wherein the end zone, transition zone, and shaft zone comprise a non-circular cross section.

4. The system of claim 1, wherein the shaft zone has a larger cross-sectional area than the end zone.

5. The system of claim 1, wherein the proximal end of the nail has a round cross-section.

6. The system of claim 1, wherein the nail comprises an anterior surface sized and configured to face an anterior side of the clavicle bone and a posterior surface sized and configured to face a posterior side of the clavicle bone, and wherein the nail is bent or curved toward either the anterior surface or the posterior surface.

7. The system of claim 6, wherein at least a portion of either the anterior surface or the posterior surface is flat.

8. The system of claim 1, wherein the distal end of the nail has at least one sharp edge.

9. The system of claim 1, wherein the end zone comprises a cutting geometry configured to create a path through the medullary canal of the bone, the cutting geometry comprising a curvature on at least one edge of the end zone toward the distal end of the device configured to create a sharp distal end.

10. The system of claim 1, wherein a distal portion of the nail has a cross-section with four flat sides.

11. The system of claim 1, wherein a transition zone is configured to provide at least one transitional cross section between the first cross-section with a plurality of flat surfaces and the second cross-section with a single flat surface.

12. The system of claim 1, further comprising an end cap at or configured to engage the proximal end of the nail.

13. The system of claim 12, wherein the proximal end of the nail is externally threaded and a distal portion of the end cap is internally threaded for attachment to the externally threaded proximal end.

14. The system of claim 12, wherein the end cap comprises a plurality of retractable and expandable wings for engagement with bone.

15. The system of claim 12, further comprising one or more locking screws for engagement with the end cap or the nail.

16. The system of claim 1, wherein the nail comprises a plurality of transition zones.

17. The system of claim 1, wherein the nail comprises a plurality of transition zones, with a transition zone on either end of the shaft zone.

18. The system of claim 1, wherein the nail comprises a plurality of transition zones within the shaft zone.

19. The system of claim 1, wherein the transition zone has a length of approximately 10 mm.

20. The system of claim 1, wherein the transition zone has a gradually changing cross sectional shape wherein no point is more rounded or circular than the immediate most proximal or trailing zone.

21. The system of claim 1, wherein the transition zone is a gradually changing cross sectional shape that can be achieved by simply rounding flat surfaces away from a center line of the nail.

* * * * *